(12) United States Patent
Jenkins

(10) Patent No.: US 11,402,363 B2
(45) Date of Patent: Aug. 2, 2022

(54) SYSTEM AND METHOD FOR MONITORING WATER TREATMENT SYSTEMS

(71) Applicant: Jentek Water Treatment, Inc., Dallas, TX (US)

(72) Inventor: Mark J. Jenkins, Fairview, TX (US)

(73) Assignee: Jentek Water Treatment, Inc., Dallas, TX (US)

( * ) Notice: Subject to any disclaimer, the term of this patent is extended or adjusted under 35 U.S.C. 154(b) by 0 days.

(21) Appl. No.: 16/927,400

(22) Filed: Jul. 13, 2020

(65) Prior Publication Data

US 2020/0340967 A1 Oct. 29, 2020

Related U.S. Application Data

(63) Continuation of application No. 16/186,986, filed on Nov. 12, 2018, now Pat. No. 10,712,327, which is a
(Continued)

(51) Int. Cl.
*G01N 33/18* (2006.01)
*C02F 1/00* (2006.01)
(Continued)

(52) U.S. Cl.
CPC .............. *G01N 33/18* (2013.01); *B01D 17/12* (2013.01); *B01D 21/30* (2013.01); *C02F 1/008* (2013.01);
(Continued)

(58) Field of Classification Search
CPC ...... B01D 17/12; B01D 21/30; B01D 21/302; B01D 35/14; B01D 35/157; B01D 35/1573; C02F 1/008; C02F 5/00; C02F 2209/00; C02F 2209/001; C02F 2209/003; C02F 2209/005; C02F 2209/006; C02F 2209/008; C02F 1/68; C02F 1/685; C02F 1/686; C02F 5/08; G01N 33/18; G01N 33/1813; G01N 33/182; G01N 33/1853; G05D 7/00; G05D 7/06; G05D 7/0617; G09G 5/36; G09G 5/363; G09G 5/37; G09G 5/38;
(Continued)

(56) References Cited

U.S. PATENT DOCUMENTS 2,299,748 A 10/1942 Hatch
3,732,074 A 5/1973 Feitler
(Continued)

OTHER PUBLICATIONS

Palazzo, A., J. van der Merwe, and G. Combrink. "The accuracy of calcium-carbonate-based saturation indices in predicting the corrosivity of hot brackish water towards mild steel." Journal of the Southern African Institute of Mining and Metallurgy 115.12 (2015): 1229-1238.

*Primary Examiner* — Joseph W Drodge
(74) *Attorney, Agent, or Firm* — Frost Brown Todd LLC

(57) ABSTRACT

Methods and systems are described for monitoring and managing fluid treatment or storage systems, such as HVAC hydronic water systems. Sensors located at a fluid system can detect various types of data, such as chemical amounts, pressures, temperatures, flow rates, and more. Servers in communication with the sensors can record the data and provide it to a user in a variety of graphical interfaces. One useful interface for display of the data includes a five-sided axis called the OPTI-GON.

19 Claims, 25 Drawing Sheets

Related U.S. Application Data continuation of application No. 15/706,478, filed on Sep. 15, 2017, now Pat. No. 10,126,284.

(60) Provisional application No. 62/395,185, filed on Sep. 15, 2016.

(51) Int. Cl.

| | | |
|---|---|---|
| *B01D 21/30* | (2006.01) | |
| *B01D 17/12* | (2006.01) | |
| *G09G 5/37* | (2006.01) | |
| *G09G 5/36* | (2006.01) | |
| *G05D 7/06* | (2006.01) | |
| *C02F 1/68* | (2006.01) | |
| *F24D 19/00* | (2006.01) | |
| *C02F 5/00* | (2006.01) | |
| *F24D 19/10* | (2006.01) | |

(52) U.S. Cl.
CPC ............ *C02F 1/68* (2013.01); *F24D 19/1006* (2013.01); *F24D 19/1015* (2013.01); *G05D 7/06* (2013.01); *G09G 5/36* (2013.01); *G09G 5/37* (2013.01); *C02F 5/00* (2013.01); *C02F 2201/008* (2013.01); *C02F 2209/003* (2013.01); *C02F 2209/005* (2013.01); *C02F 2209/008* (2013.01); *C02F 2303/08* (2013.01)

(58) Field of Classification Search
CPC .......... B01F 15/00123; B01F 15/00129; B01F 15/00207; B01F 15/0022; B01F 15/00227; B01F 15/00233; B01F 15/00279; B01F 15/00285; B01F 15/00292; B01F 15/00298; B01F 15/00305; B01F 15/00331; B01F 15/00422; F24D 19/10; F24D 19/1006; F24D 19/1015; F24D 2220/04; F22D 5/00; F22D 5/26; A01G 9/247
USPC ........... 73/61.41, 61.42, 61.43, 61.44, 61.48, 73/61.59, 61.61, 64.56, 863.01, 863.02; 210/696, 739, 745, 85, 94, 96.1, 143; 422/62, 105; 436/45, 50; 700/266, 271, 700/273; 702/45, 50, 187, 188, 189; 137/2, 3, 5, 93, 551; 345/619; 366/145, 366/151.1, 152.1, 152.2, 152.4

See application file for complete search history.

(56) References Cited

U.S. PATENT DOCUMENTS

| | | | |
|---|---|---|---|
| 4,041,466 A | 8/1977 | Stuart | |
| 4,464,315 A | 8/1984 | O'Leary | |
| 4,830,757 A | 5/1989 | Lynch et al. | |
| 4,834,955 A | 5/1989 | Mouche et al. | |
| 5,779,911 A * | 7/1998 | Haug | B01D 61/12 210/143 |
| 5,859,885 A | 1/1999 | Rusnica et al. | |
| 5,895,565 A | 4/1999 | Steininger et al. | |
| 6,177,955 B1 | 1/2001 | Downen | |
| 7,506,238 B2 | 3/2009 | Dumler et al. | |
| 9,708,205 B2 | 7/2017 | Fraser et al. | |
| 10,126,284 B1 | 11/2018 | Jenkins | |
| 10,712,327 B2 | 7/2020 | Jenkins | |
| 2002/0016607 A1 * | 2/2002 | Bonadio | A61B 17/3423 606/192 |
| 2002/0067370 A1 * | 6/2002 | Forney | G06F 21/105 715/742 |
| 2002/0072922 A1 * | 6/2002 | Suzuki | G06F 16/958 709/219 |
| 2002/0117430 A1 | 8/2002 | Navarro et al. | |
| 2003/0116487 A1 * | 6/2003 | Petersen | B01D 61/20 210/85 |
| 2008/0109175 A1 | 5/2008 | Michalak | |
| 2008/0202216 A1 * | 8/2008 | Campbell | G01N 35/08 73/61.41 |
| 2008/0314807 A1 * | 12/2008 | Junghanns | B01D 61/025 210/85 |
| 2010/0049840 A1 | 2/2010 | Chang | |
| 2010/0245103 A1 | 9/2010 | Plaisted et al. | |
| 2011/0304475 A1 | 12/2011 | Higgins et al. | |
| 2013/0048745 A1 | 2/2013 | Johnson, Jr. et al. | |
| 2013/0144653 A1 | 6/2013 | Poe et al. | |
| 2014/0048244 A1 | 2/2014 | Wallace et al. | |
| 2014/0076305 A1 | 3/2014 | Jackman | |
| 2014/0113819 A1 * | 4/2014 | Niksa | C01B 13/0214 504/151 |
| 2014/0373926 A1 | 12/2014 | Jha et al. | |
| 2015/0291993 A1 | 10/2015 | Vela et al. | |
| 2016/0052798 A1 | 2/2016 | Downs et al. | |
| 2016/0212948 A1 * | 7/2016 | McGuire | C02F 9/00 |
| 2017/0212536 A1 | 7/2017 | Potucek et al. | |

* cited by examiner

FIG. 6

JENTEK WATER TREATMENT, INC.
WATER.CHEMISTRY.ENGINEERING
TOTAL WATER SOLUTIONS

Company: Demo site 1  Date 6/07/2016
Attention: John Doe
Address:

TEST RESULTS

| Water System (Sample Point) | Alkalinity pAlk | Alkalinity Total | Chlorides | Total Hardness | Conductivity (mmhos) | Cycles | pH | PO4 | CFU /mL | NO2 |
|---|---|---|---|---|---|---|---|---|---|---|
| Raw Water | 0 | 30 | 25 | 70 | 214 | | 8.28 | | | |
| Tower Limits | x | 500 | 500 | 700 | x | 5.0 | x | 1-4 | | |
| Tower Water | 10 | 13 | 110 | 400 | 1050 | 4.4 | 8.31 | 1.83 | | |
| Water Meters | | | Previous | Today | Difference | Evap | Savings | | YTD Savings | |

Conductivity Min: 1160 || Max: 1345.1 || Avg: 1230.1

Temperature Min: 73.5 || Max: 82.9 || Avg: 78.4

Steel Corrosion Min: 0.768 || Max: 1.181 || Avg: 0.922

Copper Corrosion Min: 0.079 || Max: 0.086 || Avg: 0.082

Chemical 1 Min: 6.312 || Max: 6.545 || Avg: 6.434

1) Performed water tests and all within normal range
2) Inspected cooling tower and noticed increased scaling from last visit
3) Filed on site chemicals
4) Replaced feed pump on Chemical 2

| Demo Area 1 ▼ | Demo Site 1 |
| Battlefield View (Home/Battlefield) | Contact us (/Home/Contact/c8c...) |
| Demo Site 1 ▼ | Site Contacts:<br>John Doe<br>Property Manager — 1320<br>jd@pm.com<br>555-555-5555 |

Bacterial Level — 1330

Status Indicator:

Last Service: 6/30/2016
Next Service: 7/31/2016

Chemical Inventory — 1340

| Live Stream | Savings | Reports | Data logs | Alarms | Cases | Literature |

| Number | Title | State | Created On | Priority | Description | Modified on |
|---|---|---|---|---|---|---|
| CAS-0029-G3X3V8 | Case New Grid test updated | Active (In Progress) | 9/07/2016 09:30:10 | High | Testing new grid on portal. Updated | 9/08/2016 02:39:22 |
| CAS-0001-H1R1NS | Part of BC12 | Active (In Progress) | 6/14/2016 05:30:17 | Normal | $100 | 8/29/2016 10:16:16 |
| CAS-0017-Z6F6H3 | bla-bla | Active (In Progress) | 7/22/2016 04:45:16 | Normal | | 7/22/2016 04:54:16 |
| CAS-0013-HSLST1 | Sensor 3 for Demo site 1 | Active (In Progress) | 7/13/2016 11:19:42 | Normal | New alarm sensor 3 was recorded | 7/13/2016 11:19:42 |
| CAS-0010-C3RBS1 | Sensor 3 for Demo site 1 | Active (In Progress) | 7/11/2016 08:21:54 | Normal | New alarm sensor 3 was recorded | 7/11/2016 08:21:54 |
| CAS-0009-YSP8J | Sensor 3 for Demo site 1 | Active (In Progress) | 7/10/2016 08:15:21 | Normal | New alarm sensor 3 was recorded | 7/10/2016 08:15:21 |
| CAS-0008-V7NSR2 | Sensor 3 for Demo site 1 | Active (In Progress) | 7/08/2016 05:40:08 | Normal | New alarm sensor 3 was recorded | 7/08/2016 05:40:08 |
| CAS-0006-M3B9D4 | Sensor 3 for Demo site 1 | Active (In Progress) | 7/06/2016 10:28:28 | Normal | New alarm sensor 3 was recorded | 7/06/2016 10:28:28 |
| CAS-0005-N9Z0X7 | Sensor 3 cleared for Demo site 1 | Active (In Progress) | 7/05/2016 16:42:25 | Normal | Alarm cleared. Test update from portal | 7/05/2016 17:15:28 |
| CAS-0003-Q3B5VO | Alarm for Demo site 1 X-SPECT | Active (In Progress) | 7/05/2016 14:17:27 | Normal | A new alarm has been recorded | 7/05/2016 14:17:27 |

1350

© Copyright 2016 Jentek Water Treatment, Inc. All Rights Reserved. Confidential and proprietary.

WATER TREATMENT, INC.

WATER.CHEMISTRY.ENGINEERING
TOTAL WATER SOLUTIONS

OPTI-GON REPORT

| Company: | Demo site 1 | Date: 8/22/2016 |
|---|---|---|
| Attention: | John Doe | |
| Address: | | |
| Copy | | |

1710  TEST RESULTS

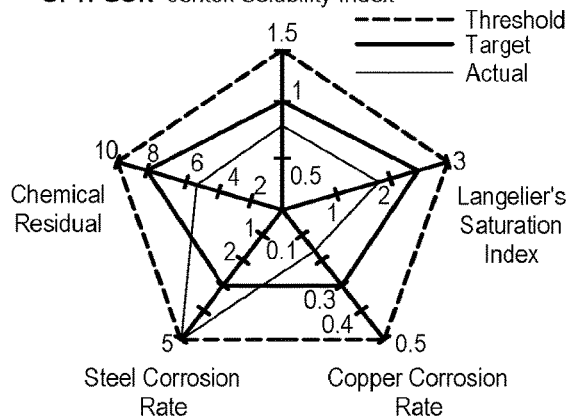

| Date Range: | 5/21/2016-7/28/2016 |
|---|---|

| AXIS | VALUE |
|---|---|
| Jentek Solubility Index (JSI) | 0.82 |
| Langelier's Saturation Index (LSI) | 1.79 |
| Copper Corrosion | 0.16 |
| Steel Corrosion | 4.84 |
| Chemical Residual | 2.82 |

Test comments for 8/22/16
Lets see if color works.
Now lets see if these comments show up in the report.

Accepted by:                Serviced by:

*FIG. 17*

1800
WATER TREATMENT, INC.
WATER.CHEMISTRY.ENGINEERING
TOTAL WATER SOLUTIONS
OPTI-GON REPORT
| Company: | Demo site 1 | Date: 7/29/2016 |
|---|---|---|
| Attention: | John Doe | |
| Address: | | |
| Copy | | |
1810      TEST RESULTS
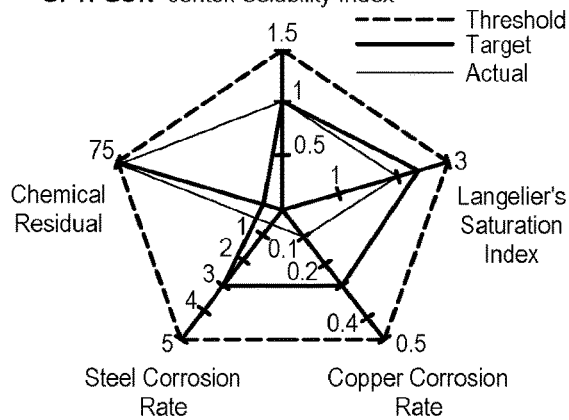
Date Range:
| AXIS | VALUE |
|---|---|
| Jentek Solubility Index (JSI) | 0.92 |
| Langelier's Saturation Index (LSI) | 2.15 |
| Copper Corrosion | 0.09 |
| Steel Corrosion | 0.45 |
| Chemical Residual | 75 |
Accepted by:      Serviced by:
*FIG. 18*

SYSTEM AND METHOD FOR MONITORING WATER TREATMENT SYSTEMS

CROSS REFERENCE TO RELATED INFORMATION

This application is a continuation of U.S. patent application Ser. No. 16/186,986, filed Nov. 12, 2018, titled "System and Method for Monitoring Water Treatment Systems", now U.S. Pat. No. 10,712,327; which is a continuation of Ser. No. 15/706,478, filed Sep. 15, 2017, titled "System and Method for Monitoring Water Treatment Systems", now U.S. Pat. No. 10,126,284; which claims the benefit of U.S. Provisional Patent Application No. 62/395,185, filed Sep. 15, 2016, titled "System and Method for Monitoring Water Treatment Systems", the contents of which are hereby incorporated herein in its entirety.

TECHNICAL FIELD

The present disclosure is directed to water management and more particularly to an online cloud-based management and control system.

BACKGROUND OF THE INVENTION

Many municipalities, commercial buildings, data centers, hospitals, universities, factories, utility plants, mining operations, oil fields and other entities have water systems requiring maintenance and monitoring. Monitoring may be needed to ensure certain purity levels, to protect against deleterious effects of water, facilitate periodic cleaning, to control utilities, monitor system operating efficiencies and materials, to monitor corrosion, organic and mineral fouling, and other factors.

BRIEF SUMMARY OF THE INVENTION

One embodiment under the present disclosure comprises a system for monitoring an HVAC hydronic water system. The system can comprise: one or more sensors operable to detect one or more properties of a fluid; one or more actuators operable to effect a change in the fluid; and one or more servers communicatively coupled to the one or more sensors. The one or more servers can be operable to store historical records of the one or more properties and to compare the one or more properties to one or more predetermined values and to send a notification when a property equals a predetermined value. The system can also comprise a computing device communicatively coupled to the one or more servers and operable to provide a graphical interface to a user, the graphical interface operable to display the one or more properties. The computing device can be further operable to receive a command from a user and to transmit the command to the one or more actuators, the computing device operable to receive the notification from the one or more servers.

Another embodiment under the present disclosure comprises a method for managing a fluid system. The method can receive data from one or more sensors that are coupled to the fluid system; store the data from the one or more servers; and send a subset of data requested by a user to a computing device, the subset of data configured to be displayed in a graphical interface to the user. The method can also compare the data with one or more predetermined values; and send a notification to the computing device if the data equals a predetermined value.

Another embodiment under the present disclosure comprises a method of monitoring a fluid system. The method can comprise receiving a data set regarding one or more properties of a remote fluid system; storing the data set; creating a graphical interface comprising the data set for display to a user at the mobile device; and sending the graphical interface to the mobile device.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIG. 6 is a diagram of a possible graphical interface embodiment under the present disclosure;

FIG. 13 is a diagram of a possible graphical interface embodiment under the present disclosure;

FIG. 17 is a diagram of a possible graphical interface embodiment under the present disclosure;

FIG. 18 is a diagram of a possible graphical interface embodiment under the present disclosure;

DETAILED DESCRIPTION OF THE INVENTION

The current disclosure describes systems and methods for water or resource management, preferably in HVAC (heating, ventilating and air conditioning) hydronic water systems. A system under the present disclosure can comprise a cloud-based information repository designed to facilitate management decisions quickly and effectively with comprehensive, at-a-glance dashboards and reports. Sufficient trend analyses can be front and center with current live-stream data coupled with historical reports and "manage-by-color" according to macro and segmented by areas based upon viewing privileges. Information management in the water treatment realm has historically been pieced together from information gathered in the field at client sites as it relates to wet chemistry, control settings and equipment readings. Reports were disjointed and were located on various software making trend analyses, problem identification/resolution very difficult let alone providing the opportunity to maximize system efficiencies via optimization as defined by key performance indicators.

One embodiment of the present disclosure comprises a monitoring and management system for HVAC hydronic water systems. While certain embodiments under the present disclosure can comprise treatment and maintenance of HVAC systems, the present disclosure can be applied to numerous fluid or water treatment, maintenance, and monitoring systems. Possible embodiments could comprise boilers, chillers, storage tanks; fluid management of gas or oil in transportation trucks, vehicles, or boats; HVAC systems for vehicles or buildings; bottling operations and facilities; gas stations; water asset management for fire departments and government entities; utility plants; asset management for retailers; water or feed tanks for animals or wildlife; agriculture; farms with moisture detecting devices; and more. Embodiments can include systems and methods for facilities management. Uses can include monitoring and maintenance for mineral concentrations, corrosion rates, mineral deposition, bacterial growth and more. A management system can comprise a one-directional (or bi-directional) information stream from a water monitoring service (such as X-SPECT Total Water Performance Centers) via encrypted API language into a client-facing portal. Information is further encrypted and stored on cloud-based servers with daily back-ups. When bi-directional communication is required, it can be limited to professionals of a managing entity in order to reach system controls to adjust settings to attain desired performance characteristics. This separation of controller access prevents malicious attacks through the management system. The management system fosters the ability to identify problems, trends and frequencies of occurrences enabling a mobilized response to analytics within, or developed by, the water monitoring service.

Figure 1:
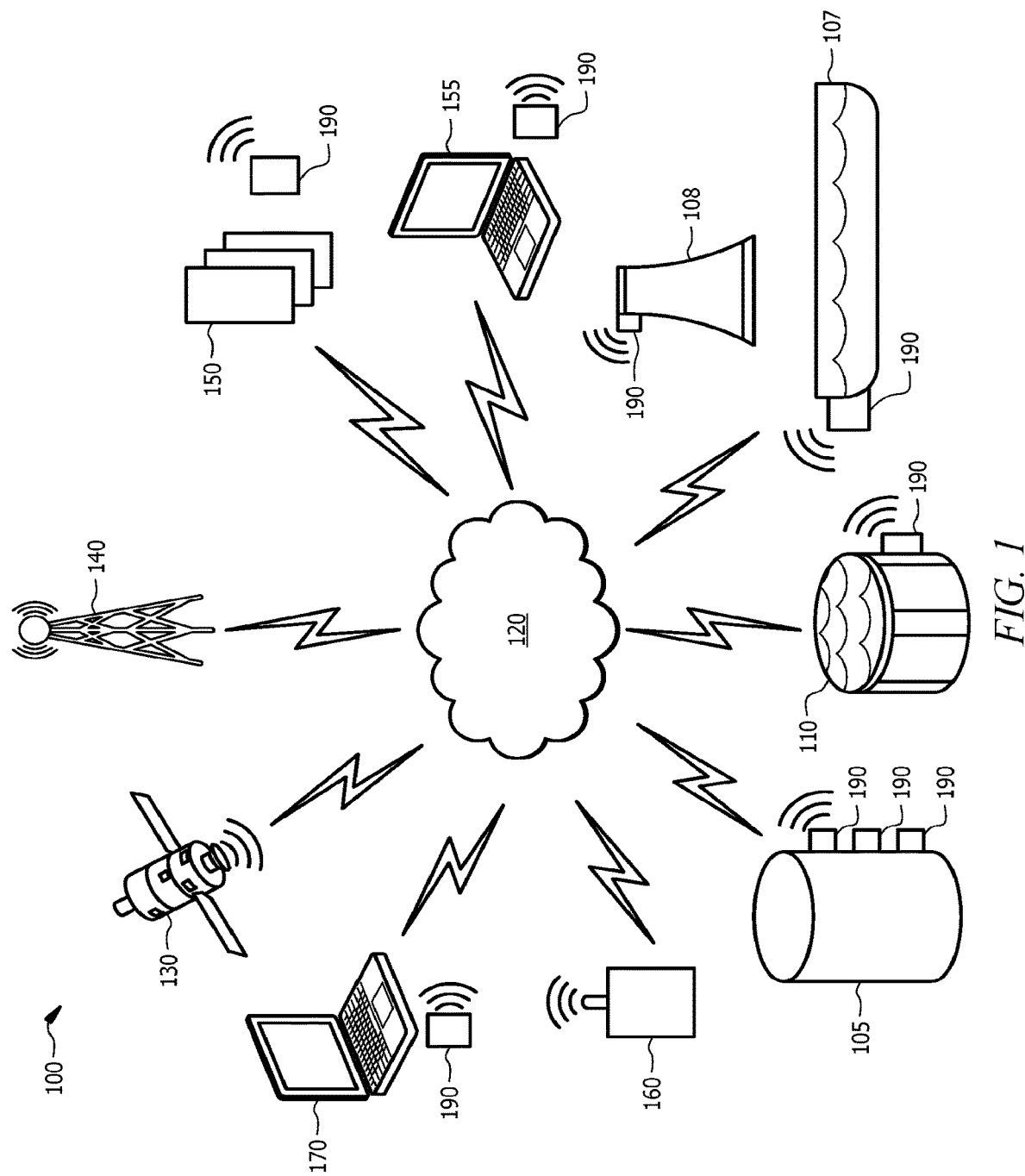
FIG. 1 is a diagram of a possible system embodiment under the present disclosure.

Referring now to FIG. 1, a system 100, incorporating elements of a possible embodiment of the present disclosure, is shown. Water systems or fluid storage elements 105, 107, 108, 110 are shown. These elements can comprise HVAC hydronic water systems 105, storage tanks 110, wells, reservoirs or pools 107, cooling towers 108, or any other storage or treatment tool for water or fluids including but not limited to hydronic, potable/non-potable, re-use or reclaimed, recreational, irrigation, waste, process, steam, fresh or salt water. Each element 105, 107, 108, 110 can comprise a variety of sensors such as sensors for conductivity, temperature, pH, ORP, specific ion, hardness, corrosion rates, chemical concentration, salinity, pressure, location, altitude, speed, humidity, moisture, pollutants, toxins, fluid level, weight, usage rates, and more. Each element 105, 107, 108, 110 can also comprise a variety of control mechanisms for directing the activities of the element 105, 107, 108, 110. Some embodiments will not use controlling mechanisms but will focus on monitoring and reporting of status. Control mechanisms can comprise valves or pumps that release, circulate or inject water and/or other substances or chemicals, valves that direct water/fluid through a filtering, sampling or other process, controls for pressure, temperature, or other properties, injection pumps, and more. These sensors and control mechanisms can be networked together via a local connection or server/computer, or individually linked directly to a communication network 120, such as the internet. Communication between sensors/controls and the communication network 120 can be wireless via satellite 130, cellular service 140, other wireless technologies, radio or by wired communications, or any combination of the foregoing. In communication with the sensors and storage elements are a plurality of servers 150 and/or computers 155. Servers 150 and computers 155 can be individually linked to network 120 or they can be coupled together and then share a connection to network 120. In some embodiments servers 150 can also comprise a computer interface. In some embodiments computers 155 can also comprise servers. In some embodiments servers 150 receive communications from sensors but cannot communicate to control the control mechanisms. In some embodiments only the computers 155 are able to direct the activities of the control mechanisms. Mobile device 160 and computer 170 can provide an end user the ability to view the status of an element 105, 107, 108, 110. In some embodiments, mobile device 160 and computer 170 receive data from computers 155 and/or servers 150. In other embodiments, the mobile device 160 and computer 170 receive communications directly from the sensors/controls of the elements 105, 107, 108. Any water system or storage element can comprise communication radios 190 in any preferable standard such as cellular, Wi-Fi and more. Multiple radios (or hardline connections) can be used at each site or each sensor or sensor module. Other servers, hard drives, computers and equipment within the system 100 can also comprise radio interfaces. The various hard drives, computers, servers and devices disclosed can be used to notify users of alarms, conditions, status, and more. In certain embodiments, certain servers and computers will have a notification function, while different servers and computers will have responsive or controlling functions to address alarms or conditions needing attention. Functions can be divided for security purposes, so that not all functionality resides on a single server or device, for instance. Servers, computers, and devices can receive status information from systems, sites, and sensors and automatically compute action plans or responses to status, including schedules of action plans.

Elements 105, 107, 108, 110 have been described as measuring or monitoring fluids, such as water. The present disclosure could be applicable to feeding systems for cattle, other animals or wildlife. Other materials stored in containers could be monitored and managed as well.

Figure 2:
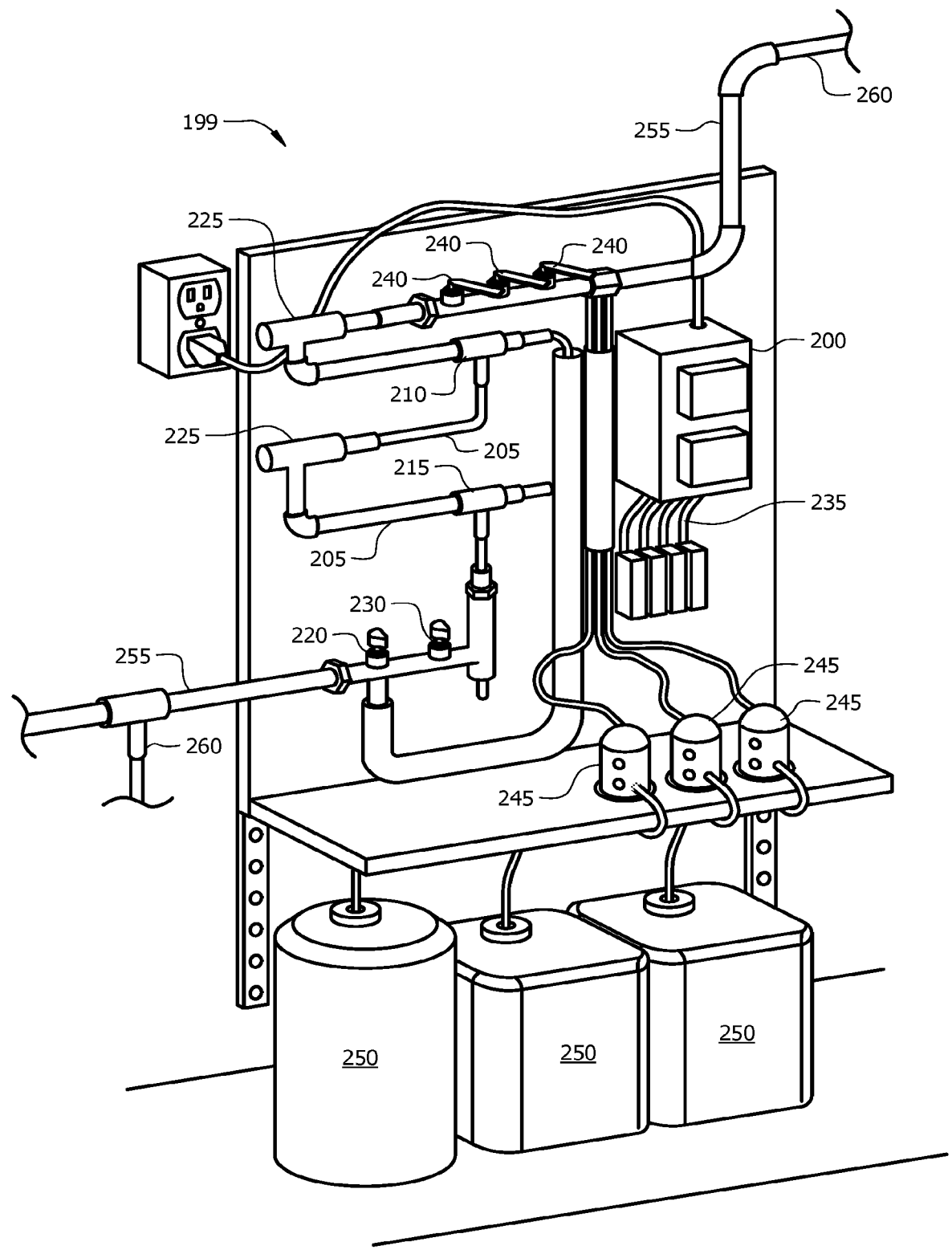
FIG. 2 is a diagram of a possible system embodiment under the present disclosure.

FIG. 2 displays an embodiment of an HVAC hydronic water system 199 under the present disclosure. Systems like system 199 could be implemented at any of elements 105, 107, 108, 110 of FIG. 1. System 199 comprises a controller 200, water 205 (or another fluid), sensors 210, 215, 220, 230, hardline or other communication connection 235, and injection points 240 with valves or pumps 245. Although a water sample stream 255 is shown, the present disclosure can comprise any type of water or fluid element. System 199 comprises performance validation corrosion coupons 225, sensors 210, 215, 220, 230 (a system can comprise any number of necessary sensors) that can be in communication with a network, such as shown in FIG. 1. The connection can be via a hardline 235 or via a wireless interface on one or all of the sensors 210, 215, 220, 230 or to the controller 200. Fluid 205 can comprise water or another fluid. Pipes 255 and valves 260 can be used to direct fluid/water away or to the system 199. Injectors or valves 240 can also be used to add or subtract other substances, such as cleaning agents or certain desired chemicals 250. Pipes 255 and 260 can also be used to supply water/fluid 205 to another location, such as a process, building or water supply. Pipes 255 and valves 260 can also be used to direct water/fluid 205 to a treatment or testing process.

One benefit under the present disclosure is the ability to graphically convey important information regarding a HVAC hydronic water system or other type of supply or treatment system. This can allow untrained personnel to understand and work with the system. The present disclosure can provide management tools, trend analysis, function verification, status updates, alarms, map views, and more. Some of these elements can be color coded to allow users to quickly be notified of alarms, or for instance to see a map view and have certain sites color coded to convey safe or alarm conditions. The present disclosure can provide many different options for management by visualization. Embodiments under the present disclosure can also provide for remote management and control of water or fluid supply and treatment systems.

Embodiments of a management system under the present disclosure can provide a livestream of high-frequency data. Such a stream increases data resolution nearly 20-fold compared to limitations within controller memory cards. Therefore, problems and trends can be magnified due to hyper-sampling (polling every five minutes compared to every 90 minutes). "Snap-line" and scrolling trend analyses can clearly identify "cause and effect" results. Stacked graphs displaying key monitoring points can be illustrated in varying colors aiding in the identification of parameters. The graphs also report high/low/average values over a selectable date range. Comparing peaks-to-valleys of sensor and meter data visually illustrates the cause and effect nature of chemical water treatment. Columns of site reports can be organized within a single tab providing efficient and comprehensive remote evaluations pertaining to on-site water performance reports, corrosion reports and bacterial reports (specifically legionella).

Figure 3:
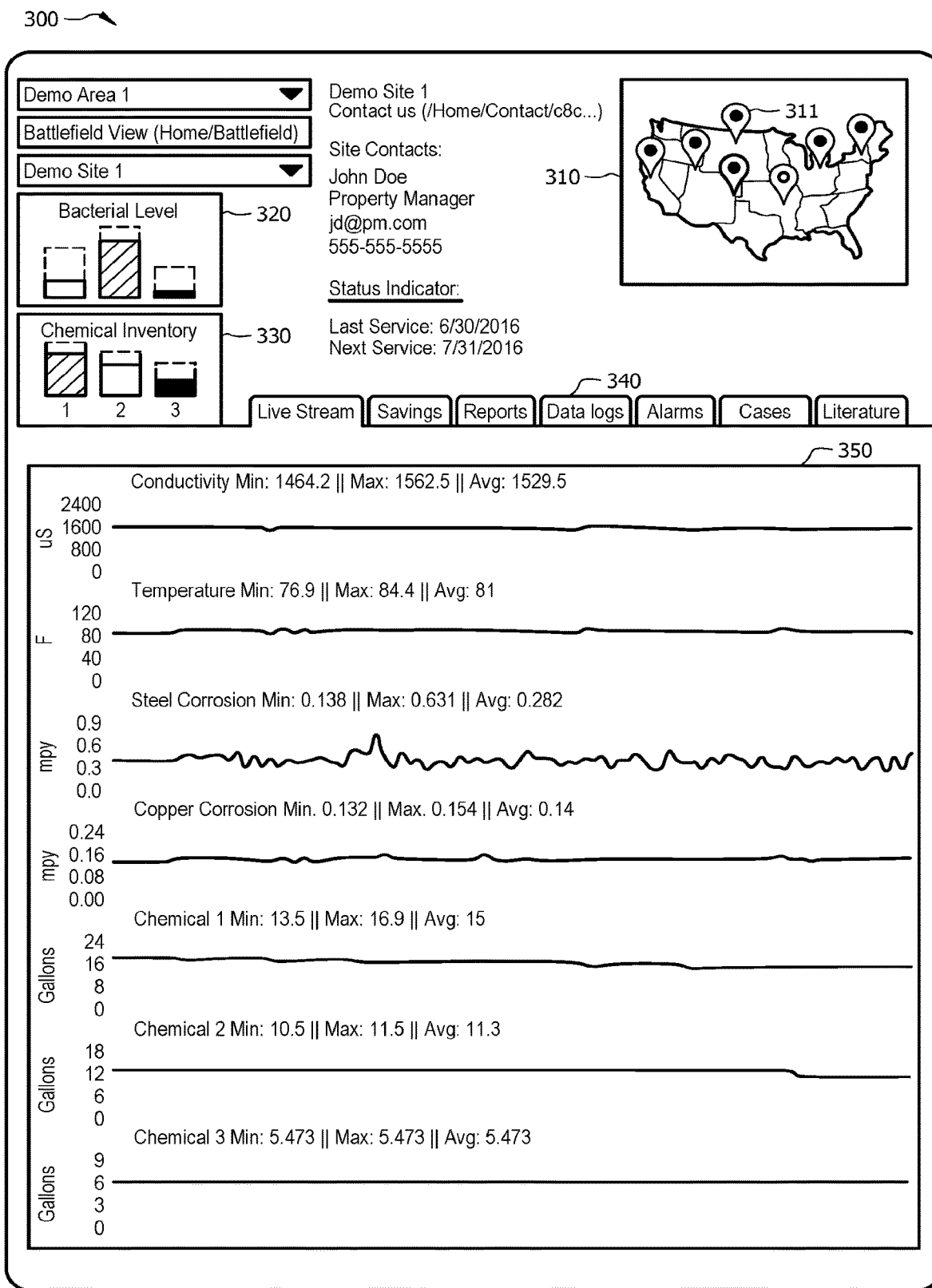
FIG. 3 is a diagram of a possible graphical interface embodiment under the present disclosure.

FIG. 3 shows an embodiment of an interface 300 for communicating data from the sensors of FIG. 1 or 2 to a user. Numerous sites can be seen on a map view 310. A user can click or hover over a location on a map to view data from that location in the interface below the map. Alternatively, a drop-down menu, or tabs, may be used to select among the available locations. Different map locations 311 can be color coded to indicate alarms or other conditions. Drop down menus allow a user to select a specific site to view detailed information such as bacteria levels 320, chemical inventories 330, and others. Tabs 340 allow a user to select different data to view. A live stream provides an up to date view of various measurements 350. In FIG. 3 the "live stream" tab is shown. Contact, address, and other information may also be displayed. Examples of data that can be tracked and analyzed include conductivity, temperature, steel corrosion, copper corrosion, chemical amounts, chemical residuals, bleed, and flow. Other data can be tracked as well. Each measurement may be recorded by an associated sensor, or by a sensor that tracks multiple measurements. Certain tabs in the interface of FIG. 3 can allow a user to run or print a report. An example embodiment of a report 600 is shown in FIG. 6. Report 600 can include test data 620, historical data timelines 630, and action items or tasks 640. FIG. 3 can show bacterial levels, chemical inventories, or other measurements against a background, outline, or shading showing industry or standard levels.

FIG. 3 can also show a status indicator which can take a color, such as green. Green can show that a site is functioning well or in good condition. If the status indicator goes red, an alarm condition could be intended. A site that is out of communication could also go red as a type of alarm condition. The color coding can assist a user to have "at-a-glance" management of his sites. A battlefield or map view can show multiple locations. The locations can be identified by a color arrow or other indicator on a map. A green indicator could indicate a healthy site, red an alarm condition. Other colors could be used.

Embodiments of the present disclosure can provide measurements and reports on bacterial control. Periods of time (between operations, or time to complete) of bacterial control data to determine system biological control and cleanliness can be recorded and/or displayed. These can be exponentially depicted against a backdrop of industry standards. Four months of results at-a-glance can be important to identify quarterly trend analyses. Similarly, embodiments of the present disclosure can record and display chemical inventory. This can provide predictive maintenance scheduling to ensure sufficient inventories are continuously available to deliver performance standards.

Figure 4:
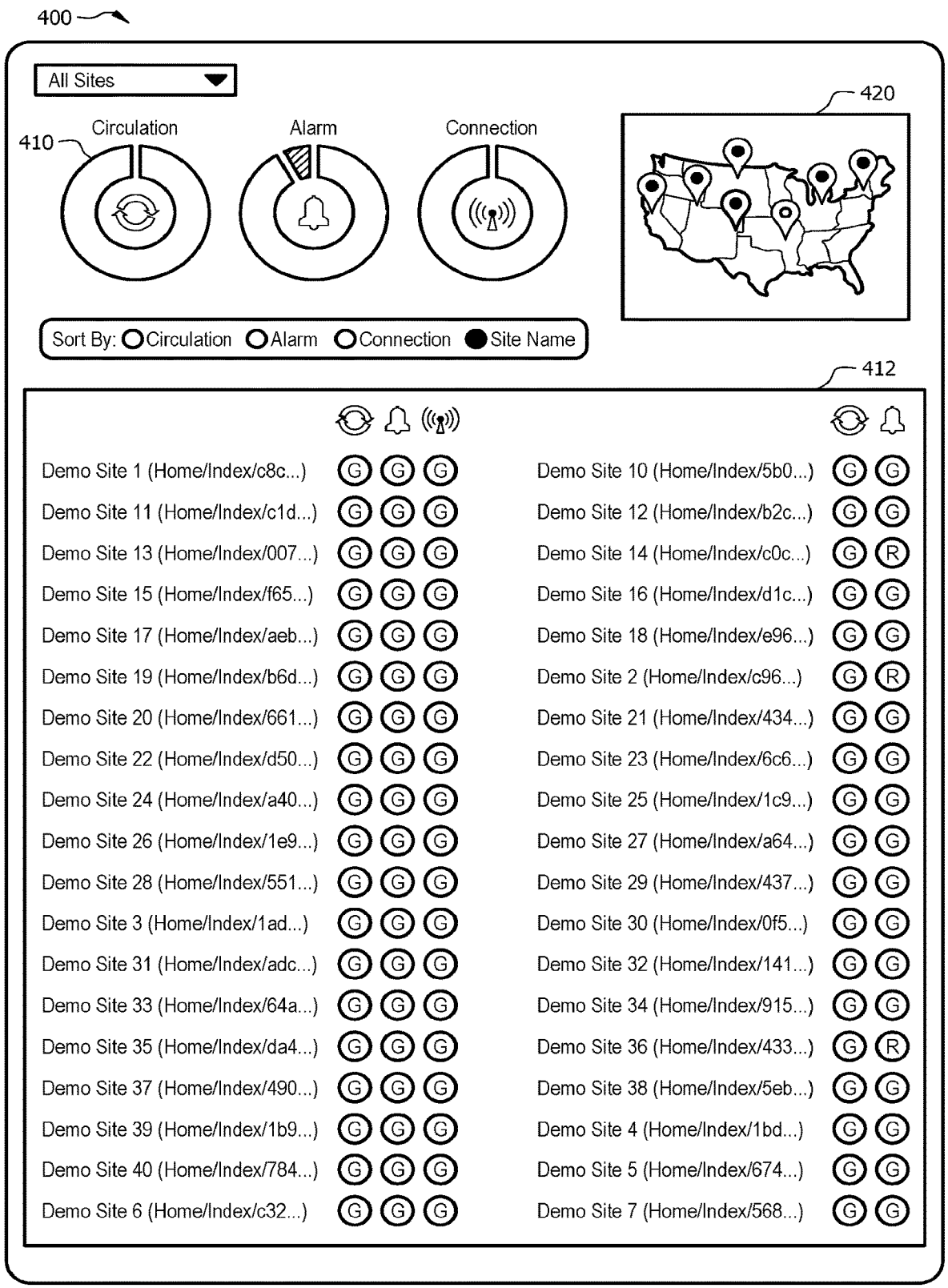
FIG. 4 is a diagram of a possible graphical interface embodiment under the present disclosure.
Figure 5:
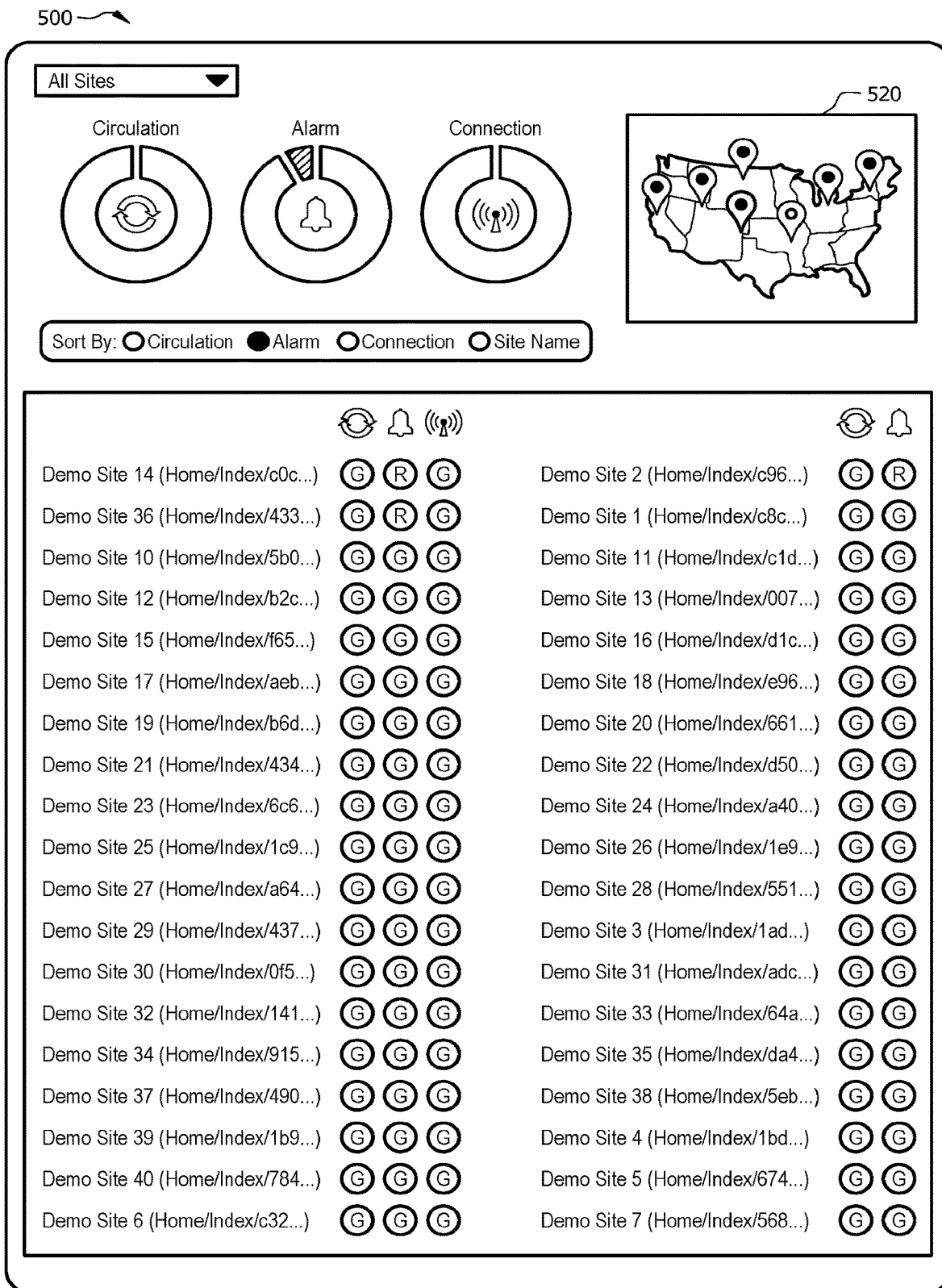
FIG. 5 is a diagram of a possible graphical interface embodiment under the present disclosure.

FIG. 4 shows an embodiment of a battlefield view 400. Battlefield view helps to provide valuable information in an easy to understand display. A map 420 can show the location of sites being monitored. Various sites are shown and a color-coded key 410, 412 shows circulation, alarm, and connection status for multiple sites. Other embodiments can replace these three conditions with other factors. Clicking on one of the columns can rearrange the data according to a different criterion, as shown in FIG. 5. Embodiments of the present disclosure can provide, track, manage, and monitor alarms. Notices of out-of-"spec" conditions can be time stamped/dated by parameter and alerted by change in site drop pin color from green to red. Users can sort alarms by date range and any combination of alarm parameters. When an alarm condition is cleared, the site indicator can revert to a green status. Embodiments of the present disclosure can comprise site indicators wherein a system(s) can be viewable by a colored drop pin on the map view. Other embodiments can comprise a satellite view, street view, or weather radar data.

Colored drop pins can take a variety of forms. Red can indicate alarms, green can represent systems are in-line, yellow can indicate an unknown cautionary status and blue can represent the current site selected. These indicators can also be viewable immediately below site contacts on the home page to prompt a quick response to site personnel and/or contacts. When observing sites from this unique point of reference, a user can be able to see their entire list of sites on a map containing colored drop pins and upon a grid indicating the status of system circulation, alarms and communication connectivity. Immediate attention may be directed to a site by clicking the corresponding map pin or grid location. Each of these items of interest can be quantified in a dashboard totalizing the number of failed site points of interest supporting at-a-glance and manage-by-color responses. Sortable features by site name, circulation, alarm or connectivity supports immediate trend analyses, resource allocations, service deployments and scheduled operating events. Functionality to address users affected by color blindness has been incorporated by placing letters within colored status indicators. For example, "G," "Y" and "R" are displayed within the Green, Yellow and Red (in-line, cautionary, alarm) status indicators for rapid management action to assign resources where they are needed instead of managing by a predetermined schedule. This unique vantage point will reduce preventative and predictive maintenance expenses.

Figure 7:
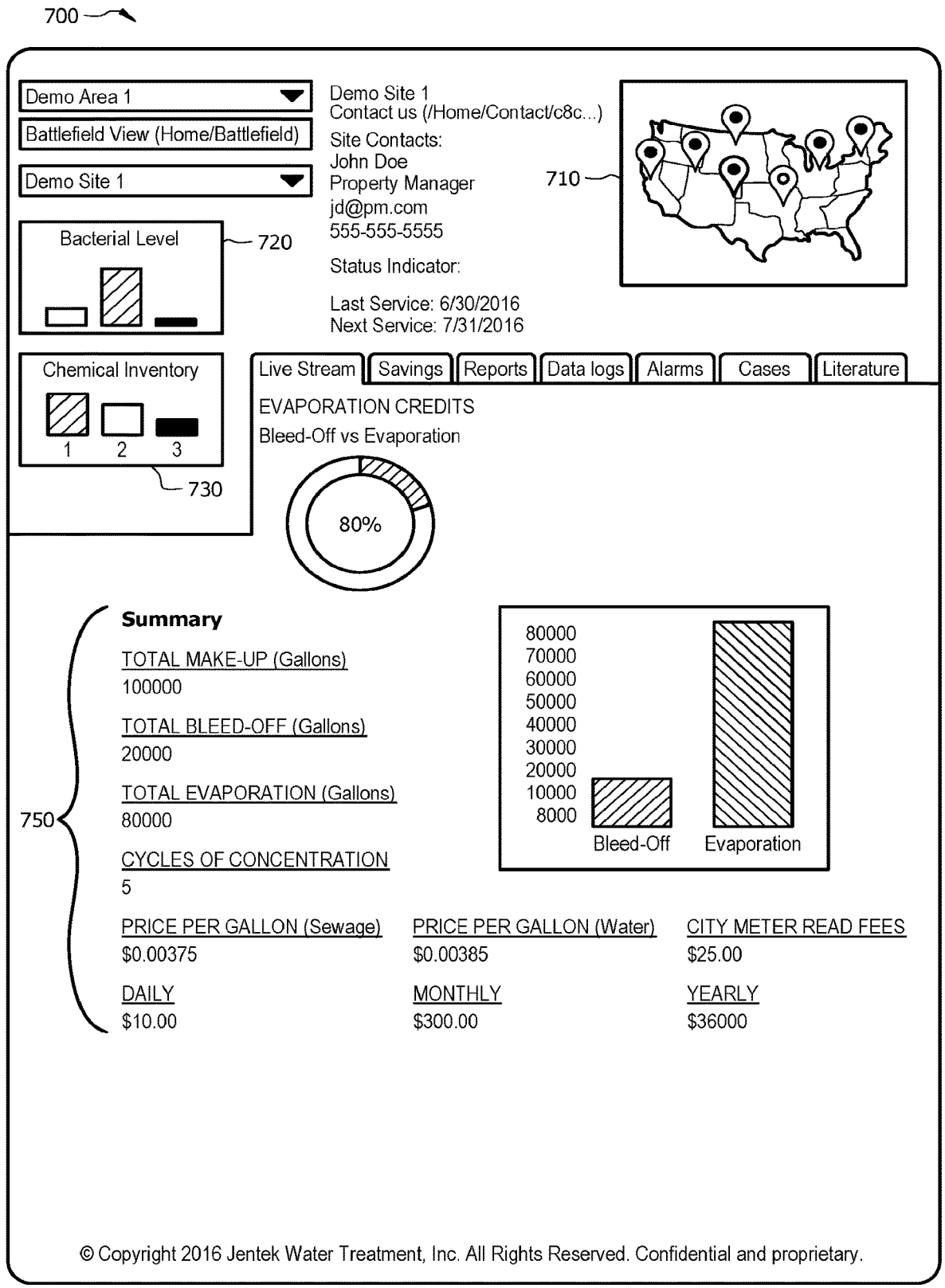
FIG. 7 is a diagram of a possible graphical interface embodiment under the present disclosure.
Figure 8A:
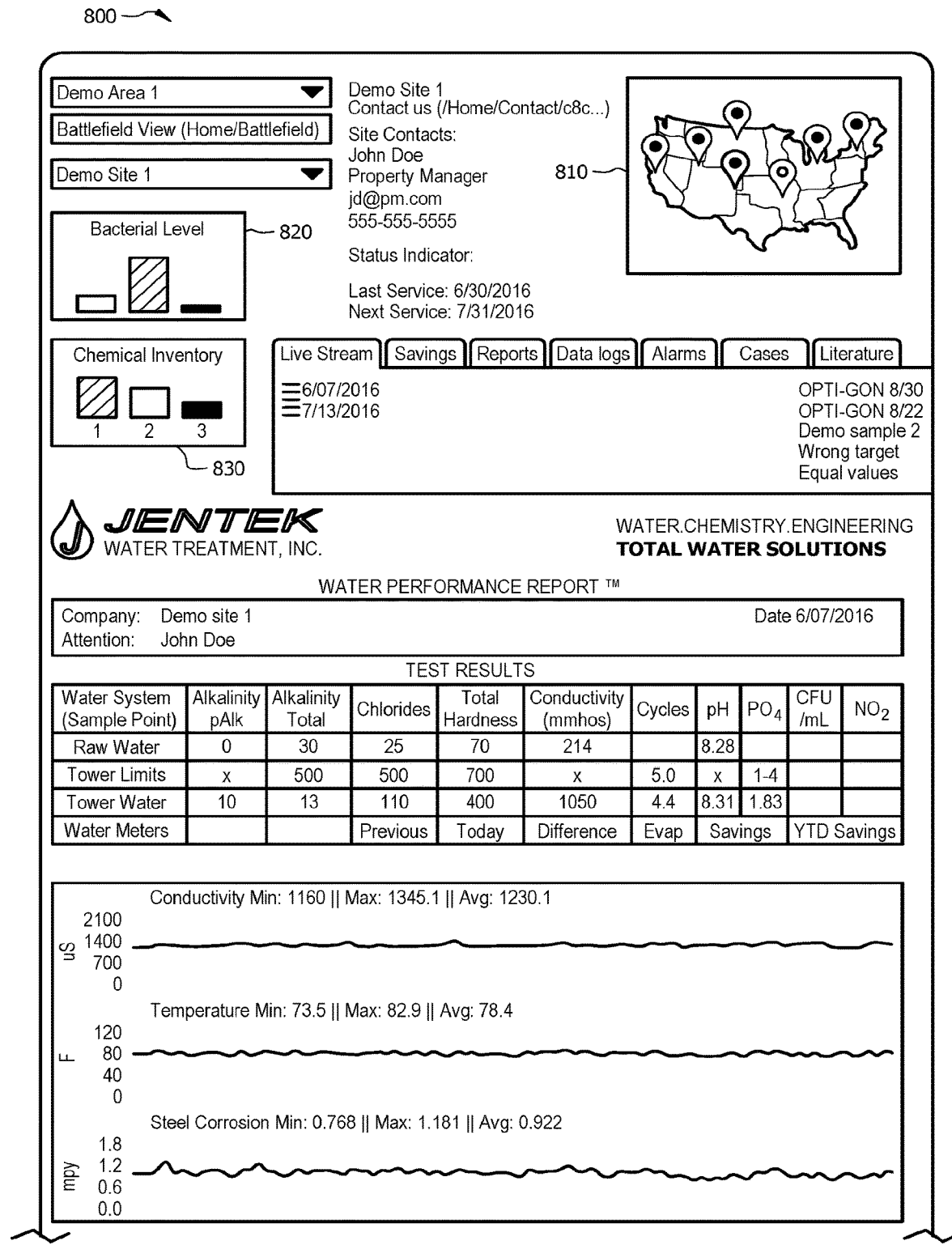
FIG. 8A-8B is a diagram of a possible graphical interface embodiment under the present disclosure.
Figure 8B:
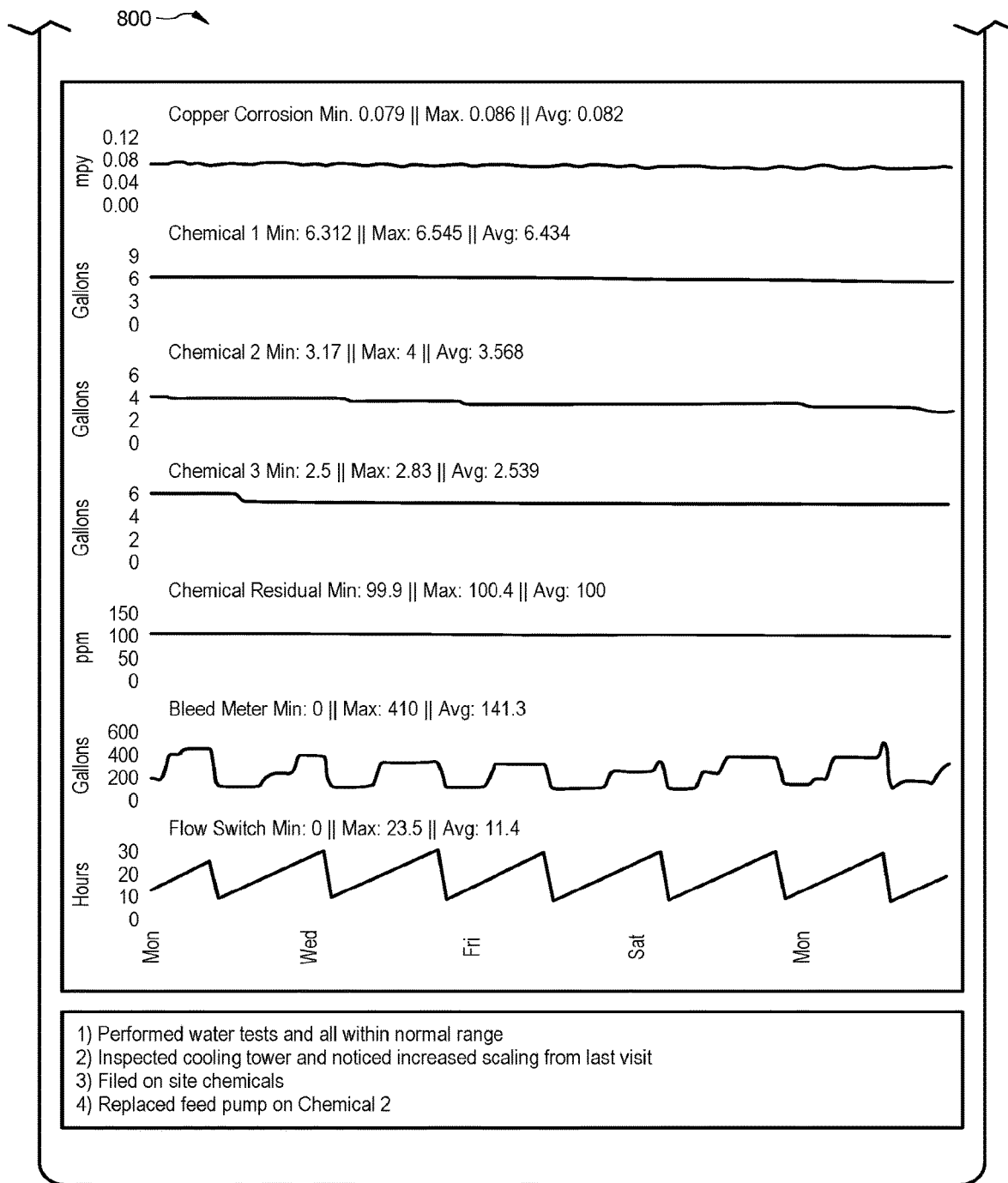

FIG. 7 shows an embodiment of an interface 700 for the savings tab. This tab shows how the system disclosed can save a user money. Tab 700 can comprise a map view 710, bacteria levels 720, chemical inventory 730 and savings data 750. Savings data 750 can comprise calculations or data regarding water or fluid usage, efficiency measurements, and other data.

Figure 9:
FIG. 9 is a diagram of a possible graphical interface embodiment under the present disclosure.
Figure 10:
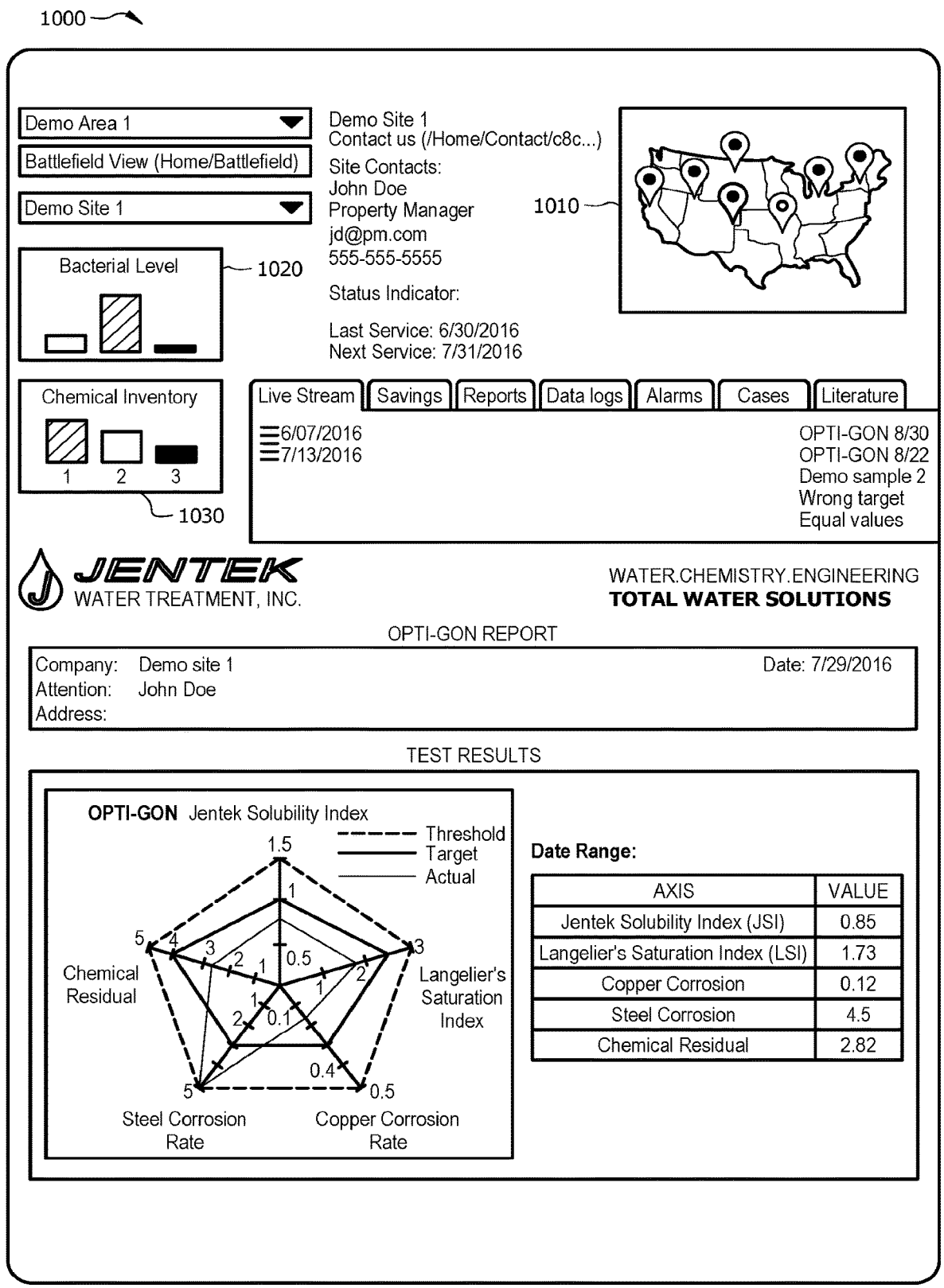
FIG. 10 is a diagram of a possible graphical interface embodiment under the present disclosure.

FIGS. 8A-10 show possible embodiments of an interface 800, 900, 1000 under the reports tab, where clicking on a hyperlink can display the report chosen. These reports can include the sample report shown in FIG. 6. FIGS. 9 and 10 show a five-axis graphical representation report called OPTI-GON (discussed further below). Reports such as 800, 900, 1000 can be saved, printed, shared or otherwise exported from the system for additional use. Such reports can provide a history of the site.

Figure 11:
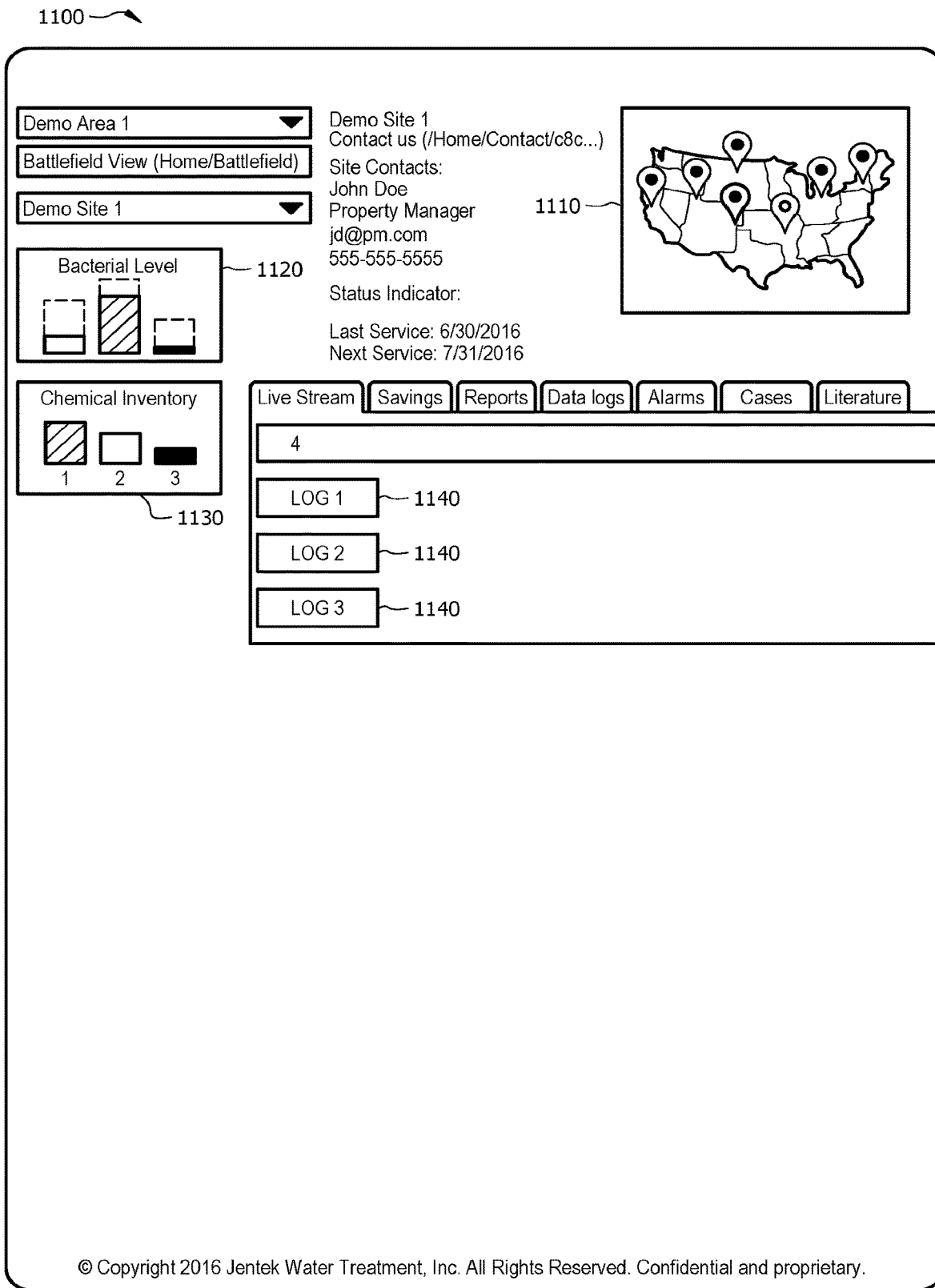
FIG. 11 is a diagram of a possible graphical interface embodiment under the present disclosure.

FIG. 11 shows a possible embodiment of an interface 1100 under a data logs tab. Here a compilation of data logs 1140 such as operator test results, chiller loads, approaches and more can be collected for access to a user. Each data log 1140, comprising either formatted data or raw data, or multiple sets of data, can be downloaded, printed, or otherwise exported for use by a user. Bacterial levels can be shown against a backdrop that shows a desired level or industry standard in a different color or shadow. Chemical inventory levels can be depicted against a backdrop that shows present levels against full container capacities.

Figure 12:
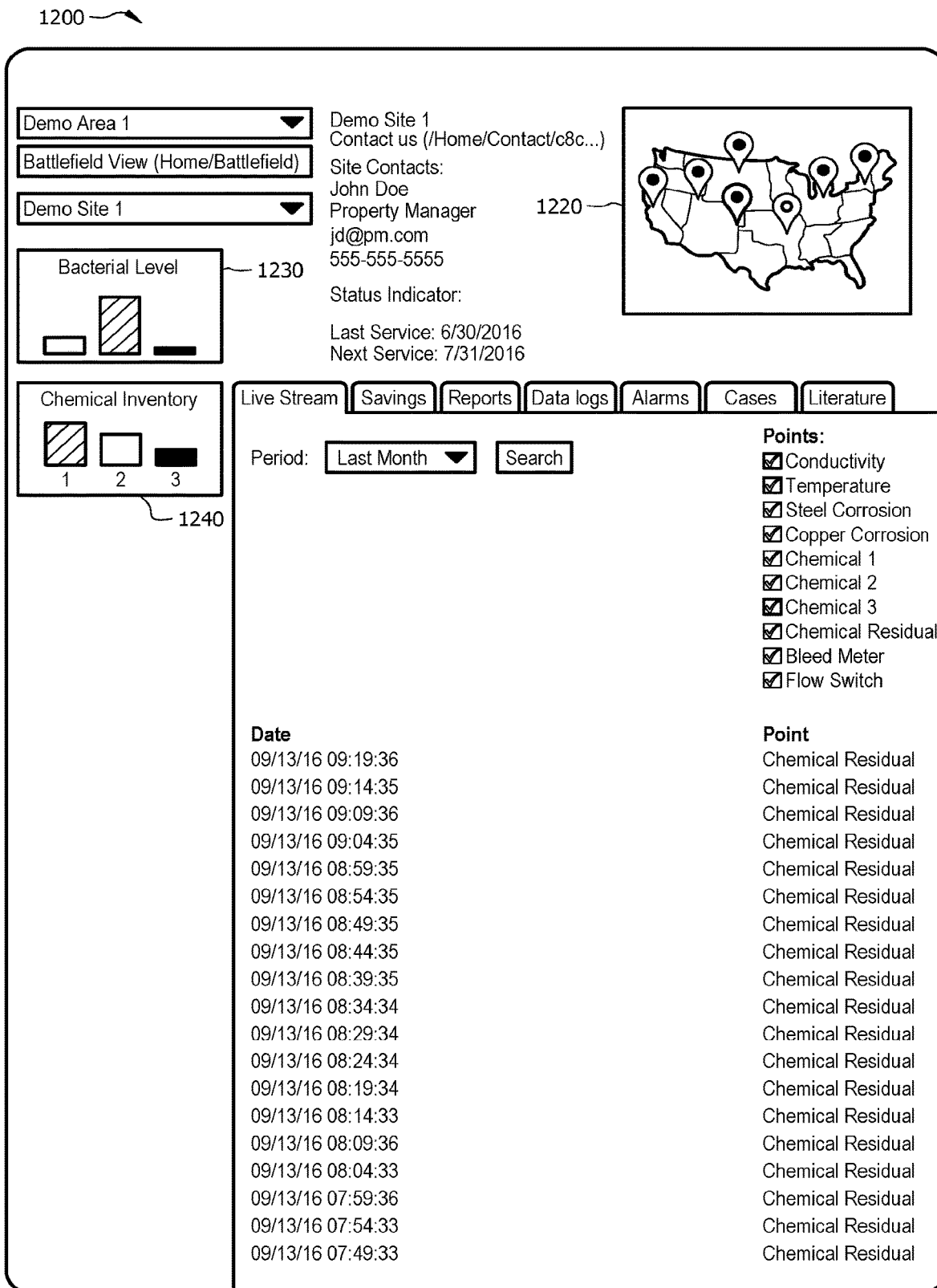
FIG. 12 is a diagram of a possible graphical interface embodiment under the present disclosure.

FIG. 12 shows a possible embodiment of an interface 1200 for the alarms tab. Here a user may view previous alarms and their location, time, date and cause.

FIG. 13 shows a possible embodiment of an interface 1300 for the cases tab. Here a user may view cases related to a site. Cases 1350 can include tests, case studies, alarm situations, or other instances saved by the system or by a user.

Figure 14:
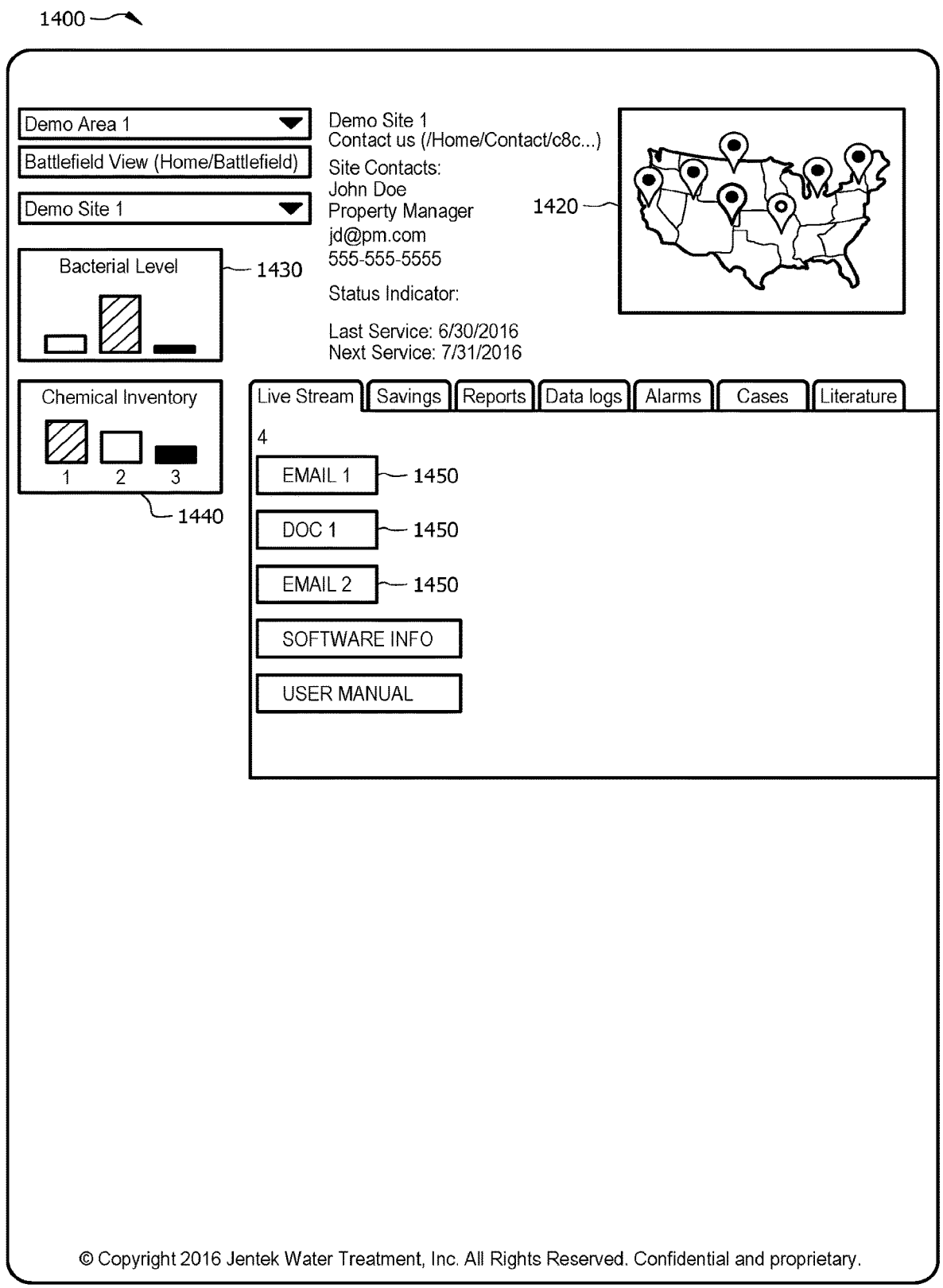
FIG. 14 is a diagram of a possible graphical interface embodiment under the present disclosure.

FIG. 14 shows a possible embodiment of an interface 1400 under the literature tab. The literature tab may contain items 1450 such as communications from a manager, software or instruction updates, user manuals, safety data sheets, certificates of insurance, or other items.

FIG. 15-20 display examples of a five-axis graph (called the "OPTI-GON" hereinafter) as described in several embodiments under the present disclosure. FIGS. 15-20 shows how the values displayed in a five-axis graph can change. The threshold, actual, and target lines can be displayed. These lines could be dashed, solid, colored, shaded, or otherwise differentiated. For example, a green line could indicate actual measurements, red could indicate threshold/alarm values, and yellow could indicate target/desired values. When an actual value is out of bounds of the target or threshold values, then an alarm may be sent or triggered. FIGS. 15-20 also show how as values change, the axes can be recalibrated and the scale of any axis adjusted as necessary. OPTI-GON graphs can be included on any interface shown in FIGS. 3-14 and can incorporate online or offline data to create the graph.

Figure 15:
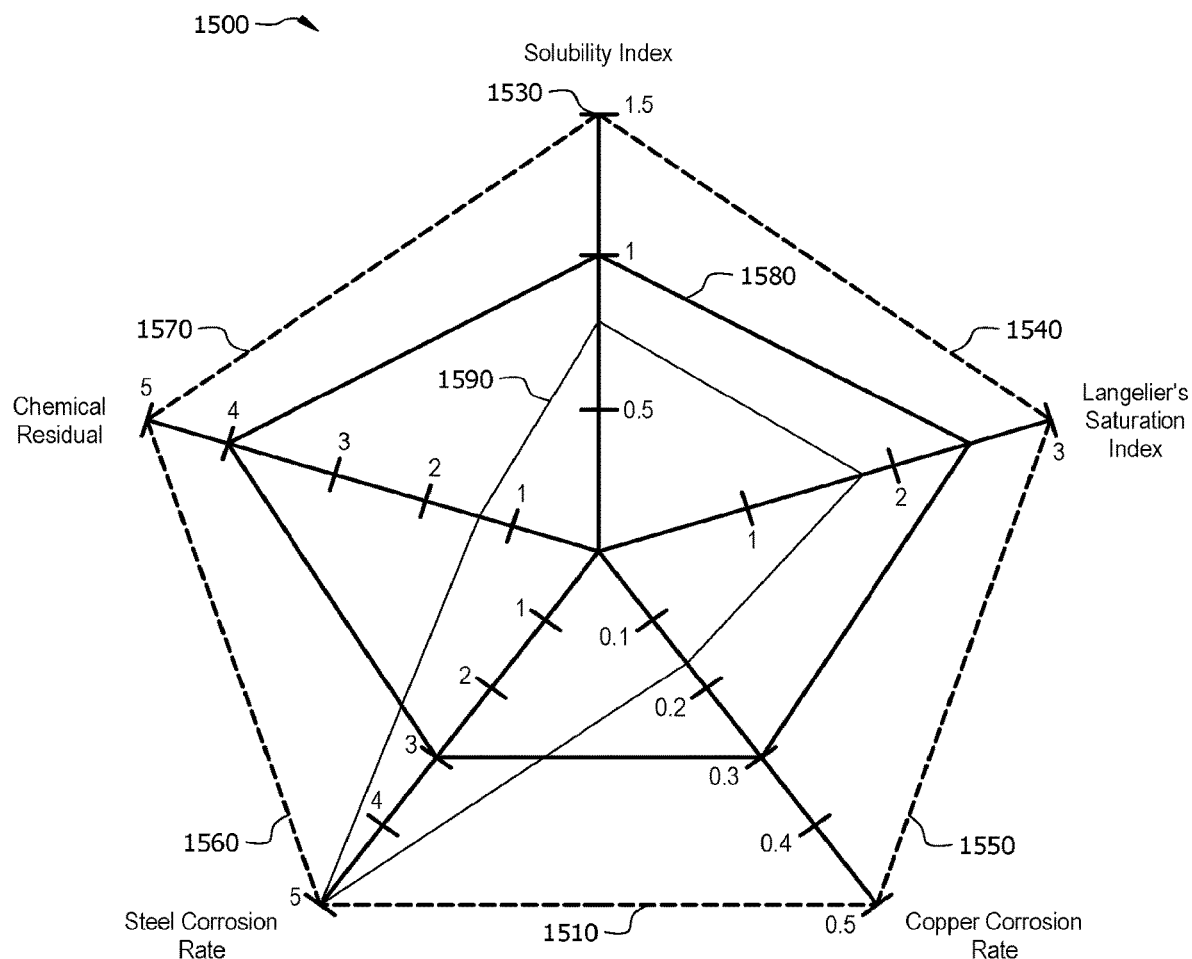
FIG. 15 is a diagram of a possible graphical interface embodiment under the present disclosure.
Figure 16:
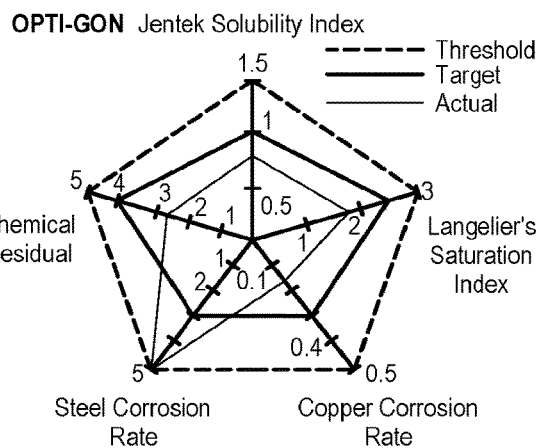
FIG. 16 is a diagram of a possible graphical interface embodiment under the present disclosure.
Figure 19:
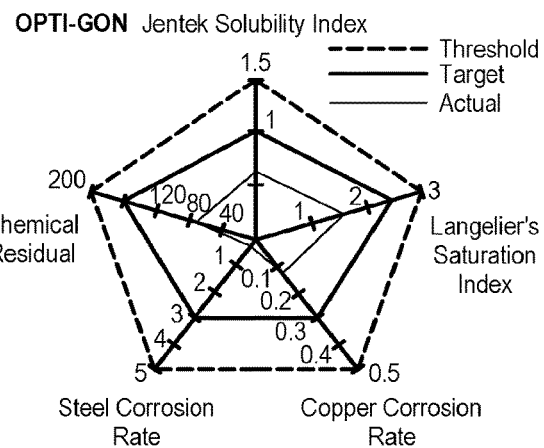
FIG. 19 is a diagram of a possible graphical interface embodiment under the present disclosure.
Figure 20:
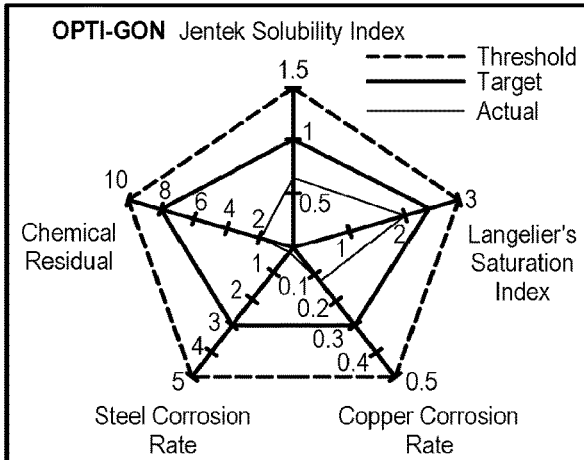
FIG. 20 is a diagram of a possible graphical interface embodiment under the present disclosure.

FIG. 15 displays a sample OPTI-GON graph 1500. In this embodiment, the five axes are solubility index 1530 (such as a proprietary Jentek solubility index), Langelier's saturation index 1540, copper corrosion rate 1550, steel corrosion rate 1560, and chemical residual 1570. Other values and measurements can also be displayed instead of these examples. Line 1510 can represent a solid red line of an outer threshold value or alarm condition for each axis 1530-1570. Line 1580 can represent a solid yellow line of a targeted value or alarm condition for each axis 1530-1570. Line 1590 can represent a dashed green line of actual values for each axis 1530-1570 of a given water supply or fluid treatment site. In the example shown in FIG. 15, the steel corrosion rate is outside the alarm condition and the system will notify a user or activate some type of alarm. In some embodiments, an alarm condition may not be an emergency and corrective measures may be taken without sounding an alarm or sending a notification. The OPTI-GON can provide a visually compelling depiction of inter-disciplinary principals of water management. It can delineate threshold, target and actual values within the same view. Five-sided representations included under the present disclosure can identify corrective adjustments to apply to attain optimization and/or problem resolution. When actual values are visualized as if knots within a connected string, each axis is capable of being reduced by increasing the polar opposite axes. The corollary applies as well; whereby, when an axis is increased in numerical value, its opposing axes follow behind its vector movement and are subsequently reduced. Actual values are designed to reside within target values and warrant significant action when approaching or exceeding threshold values.

One embodiment of a five-sided representation can be implemented as follows. Axes can be oriented in a pentagon shape with the first axis, Jentek Solubility Index. located at the approximately 12 o'clock position, Langelier's Saturation Index (also substitutable with Rynar's and Puckorius Indices) at the approximately 2 o'clock position, Copper Corrosion Rate located at the approximately 4 o'clock position, Steel Corrosion Rate at the approximately 8 o'clock position and Chemical Residual located at the approximately 10 o'clock position. Jentek Solubility Index (JSI) is used to monitor mineral solubility in circulation within an evaporative water system to ensure clean heat transfer surfaces and energy efficiency. Langelier's, Rynar's and Puckorius' indices (LSI, RSI and PSI respectively) measure water saturation thresholds and have a direct impact on water consumption and sewage discharge. The arrangement of axes in FIG. 15 is a preferred embodiment, but other layouts are possible.

Some values, such as LSI, RSI, and PSI, may require physical collection of samples of water and subsequent testing to work in conjunction with the display of other values. Corrosion rates of copper and steel represent preservation of capital equipment: heat transfer surfaces (tubes and heat exchangers), pipe, chillers, cooling towers, closed circuit coolers, evaporative condensers, air handling units and interconnected equipment. Chemical residuals are tracked as mineral scale and corrosion inhibitors must control opposing forces of mineral precipitation and corrosion. Since chemical inhibitors are customarily formulated with a combination of molecules within a given formula, a synergistic effect is realized from their aggregate presences. However, formulations vary dramatically by composition, concentration, geographical water requirements and manufacturer. One benefit of the graphical representations under the present disclosure can be the ability to adjust axis values to customize the capabilities and limitations of any formulation to attain the desired performance criteria established within target and threshold values represented by graphical representations and specified by either water treatment consultant, firm, client, engineering firm, or request for proposal (RFP). An immediate at-a-glance representation extracts complex chemical, numerical and graphical representations of data and converges them into a unique format that illustrates what conditions may be optimized to maximize system efficiencies and longevities.

A water or fluid management system under the present disclosure can collect data from a plurality of sites or locations, across numerous cities or states. A battlefield view can show numerous sites and allow a user to select one for view. The system can also coalesce usage and failure data across time and multiple locations. Data can be compared on corrosion rates, and other alarm situations. Data could be tracked on how different repair services compare to each other on quality or time efficiency. All the collected information can be used to optimize trend lines, set points, industry standard values, predetermined values or alarm conditions, and other data. For example, an alarm condition in an OPTI-GON, such as a chemical residual value, may be adjusted if historical data suggests a different value is appropriate. Artificial intelligence could be used in some embodiments. For example, the system may comprise the ability to direct the actions of controllers at each site it manages. As data is received, and possibly compared with other sites, the system can autonomously change settings at site, or change predetermined values or alarm conditions.

Figure 21:
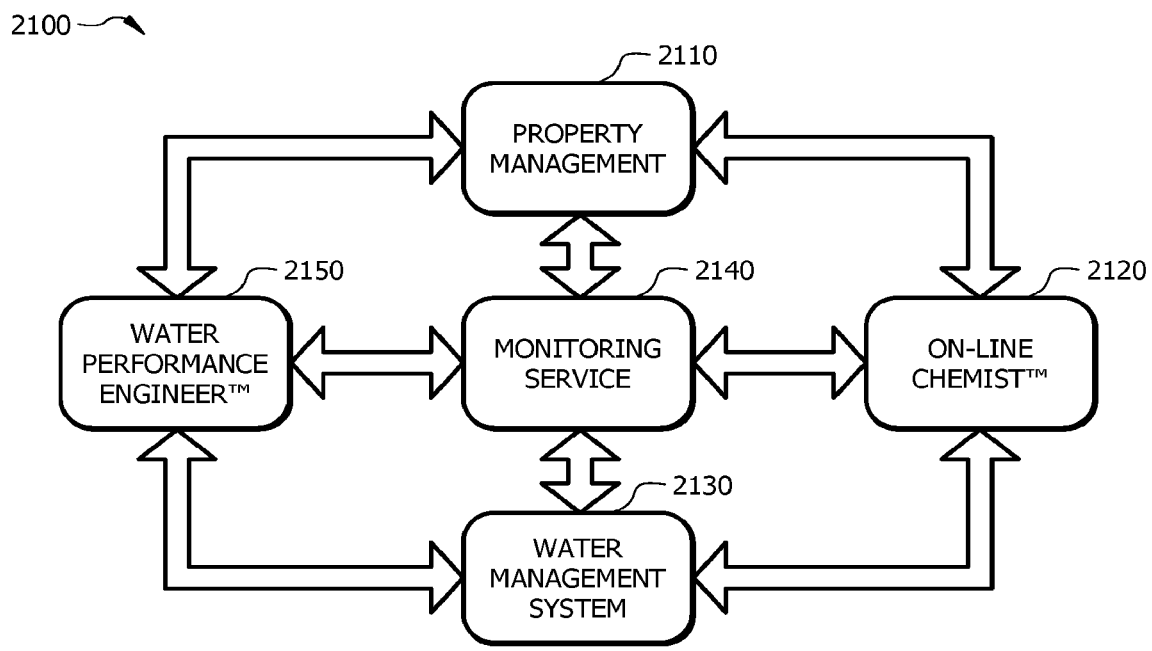
FIG. 21 is a flow chart diagram of a possible embodiment under the present disclosure.

FIG. 21 displays a possible flow chart for some embodiments under the present disclosure. Property management systems 2110 can communicate with water engineer services 2150, a monitoring system 2140 (which can comprise a software as a service system or other data hub), and an online chemist service 2120. The monitoring system 2140 can communicate with the water performance engineer 2150, property management 2110, the online chemist 2120, and a water management service, such as a HVAC hydronic water system, 2130. Water management system 2130 can comprise a plurality of valves, injection pumps, and other components in communication with a central server such as described in other embodiments under the present disclosure, such as FIG. 1. The water management system 2130 can communicate with the water performance engineer 2150, the monitoring system 2140, and the online chemist 2120. Other embodiments can use further communication abilities among the various elements.

Embodiments under the present disclosure include the ability of a user to remotely manage an HVAC hydronic water system (or other system for water or fluid storage or treatment). For example, a user in FIG. 1 at servers 150, computer 155, mobile device 160, or computer 170, may be able to interact in a bi-directional manner with any or all of elements 105, 107, 108, 110. A user may send commands (such as in response to an alarm condition) to effect changes. Commands can include turning off/on various systems or components. Such commands can include adjusting set points of controls, release of chemicals, summoning of technicians, pre/post treatment filtering processes, activation of control relays, opening/closing of valves, and more. Two-way communication from the client portal or within the water management system allows inquiries, requests, problems, notices, etc. to be initiated and the progress of resolutions tracked and edited by title, description, priority, date created/closed. On-line chemistry (or other) customer service can be catalogued through the cases function.

Figure 22:
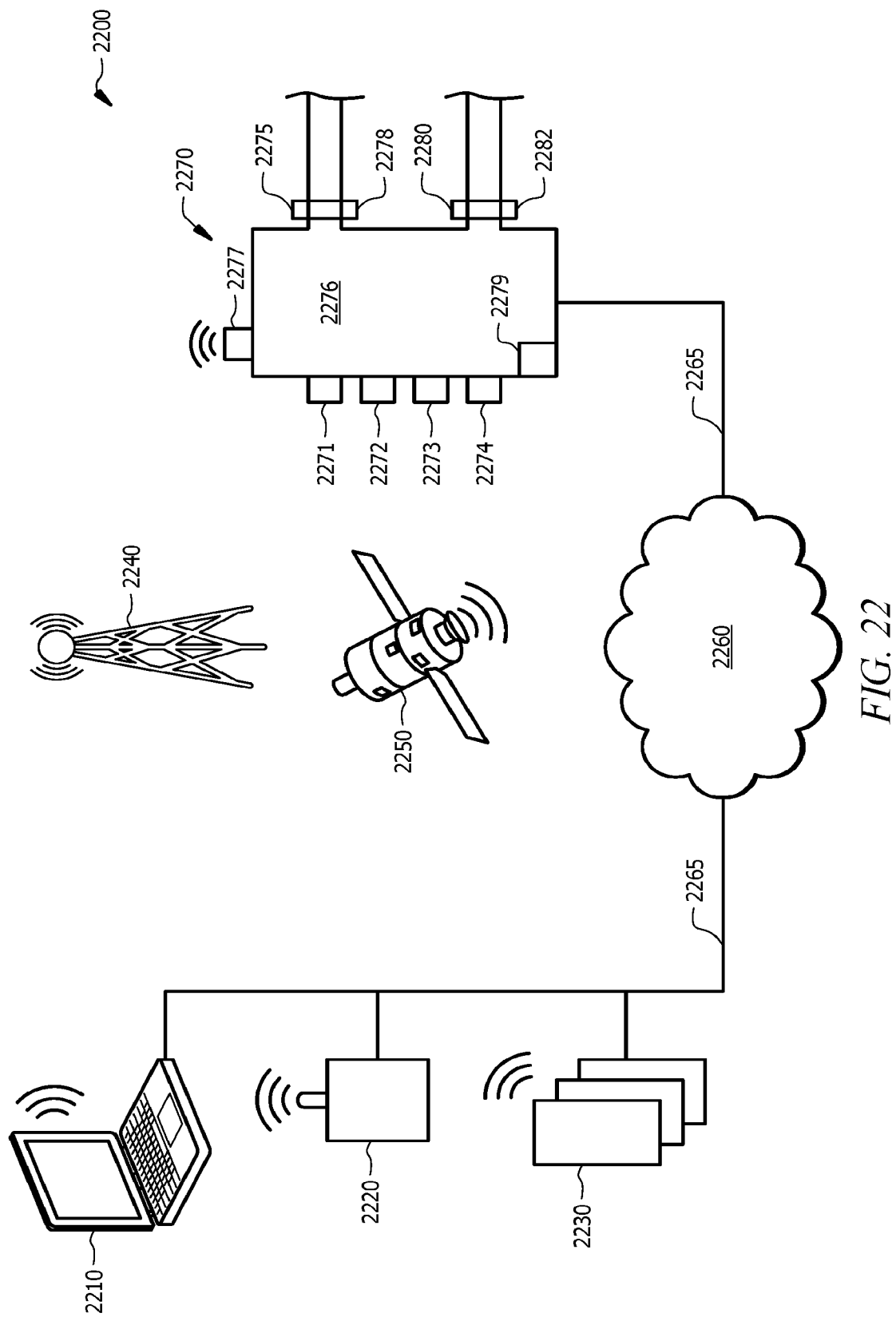
FIG. 22 is a diagram of a possible system embodiment under the present disclosure.

FIG. 22 displays another possible embodiment 2200 allowing a user to interact with a water or fluid system. A user may interact with HVAC hydronic water system 2270 by a computer 2210, mobile device 2220, or servers 2230. Devices 2210, 2220, 2230 may present a user with interfaces such as shown in FIGS. 3-20. Communication can be via hardline 2265 via a communication network 2260 (such as the internet), cellular network 2240, or other wireless network 2250 (such as satellite). System 2270 can comprise a small part of a larger fluid treatment or storage system (such as elements 105, 107, 108, 110 of FIG. 1, or system 199 of FIG. 2). Conduits 2275, 2280 can provide for transport of fluid to or from tank 2276. Valves 2278, 2282 can close and open at the command of a user. System 2270 can comprise a connection to hardline 2265 or a wireless interface 2277 for communication. System 2270 can comprise one or more interfaces 2271-2274 for adjusting or changing settings of system 2270. For example, one interface can comprise a heater/cooler for adjusting a temperature of the fluid. Another interface could control the release of materials such as cleaning agents, chemical testing materials, or other substances. This could be accomplished with injection pumps, for example. Another interface could comprise sensors for determining fluid composition, temperature, pressure, or other factors. The interfaces 2271-2274, valves 2278, 2282, wireless interface 2277, and hardline connection 2265 can all be connected to a processor 2279 that receives commands from a user at 2210, 2220, or 2230 and translates or forwards the command to the appropriate component. Processor 2279 can comprise connections to each sensor or actuator in system 2270. Alternatively, each actuator, sensor, or component can comprise an individual connection to a communication network. Actuators tend to be used for valves. When the component being controlled is not a valve it may be preferable to use a relay. Embodiments can comprise actuators and/or relays that can be controlled as appropriate depending on the component. Processor 2279 can also be responsible for notifying a user or system of an alarm condition. In some embodiments, it may be desirable to enable communication directly to a component, without the need for a processor 2279.

Servers 2230 or FIG. 22 can comprise ways for a user to interact with system 2200. In other embodiments, servers 2230 may be notified of the status of a system, such as 2270, and may issue commands to system 2270 without user input. Servers 2230 can also comprise the storage and maintenance of historical data and serve to deliver data to other users, such as computer 2210 or mobile device 2220. Such delivery of data may take the form of the interfaces shown in FIGS. 3-20.

Figure 23:
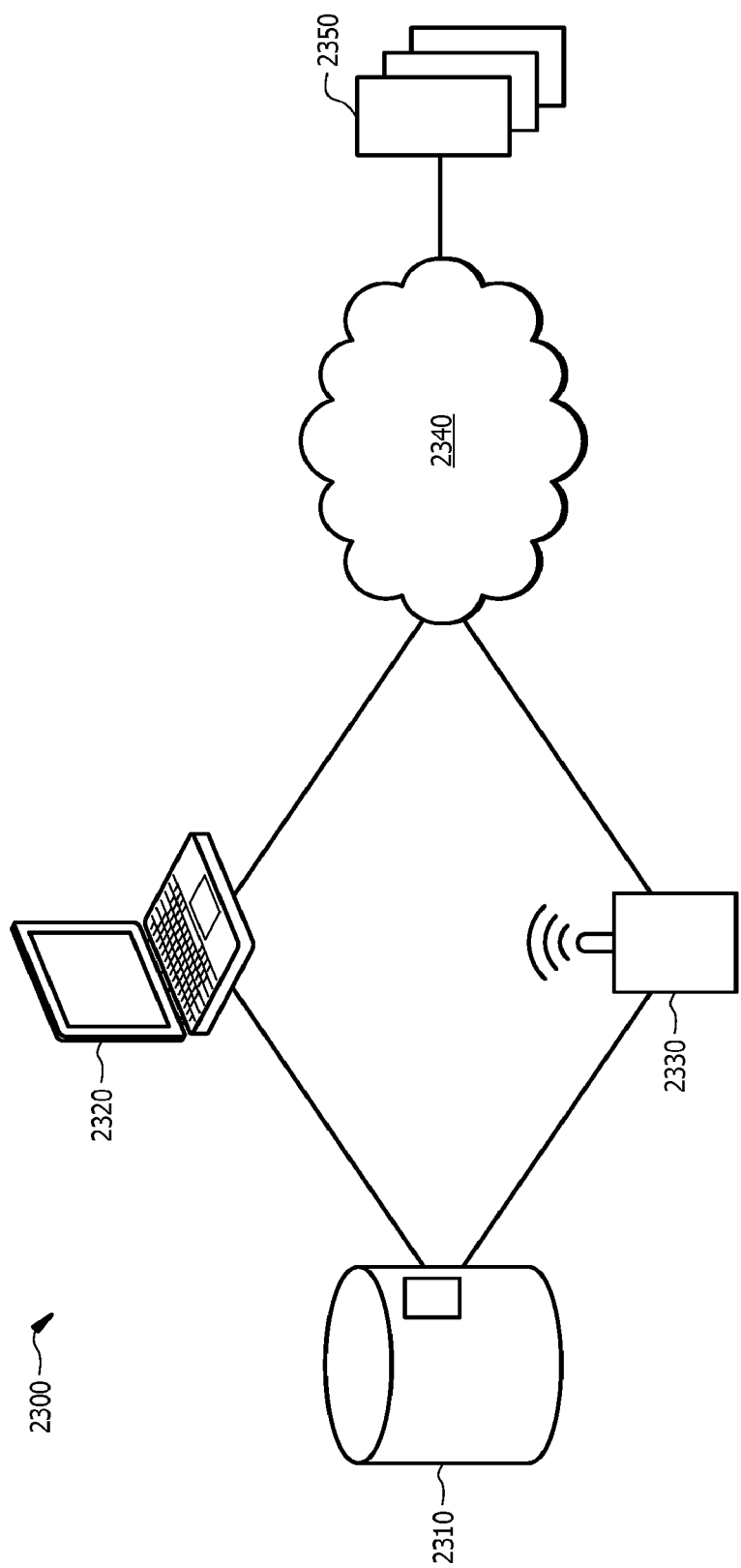
FIG. 23 is a diagram of a possible system embodiment under the present disclosure.

In alternative embodiments under the present disclosure, a computing device, such as computer 2210, mobile device 2220, computer 170, or mobile device 160, may not be affiliated, via systems 2200 or 100 with a fluid treatment or storage system. In such embodiments the computer 170, 2210, or mobile device 160, 2220 may track data regarding a third party fluid system but may have to upload data to a server, instead of the fluid system communicating directly with a server or data system. Such an embodiment can be seen in FIG. 23. Fluid system 2310 may be able to communicate (wired or wireless) with a computer 2320 or mobile device 2330 but not directly with server 2350. Computer 2320 or mobile device 2330 may track data regarding system 2310, such as fluid levels, chemical levels, temperature, and more, and then upload such data to servers 2350. Servers 2350 can analyze and chart such data, and even determine alarm conditions. Conditions may be communicated to the computer 2320 or mobile device 2330. Bi-directional communication, and the sending of commands, can be incorporated to system 2300 as described in other embodiments under the present disclosure.

Figure 24:
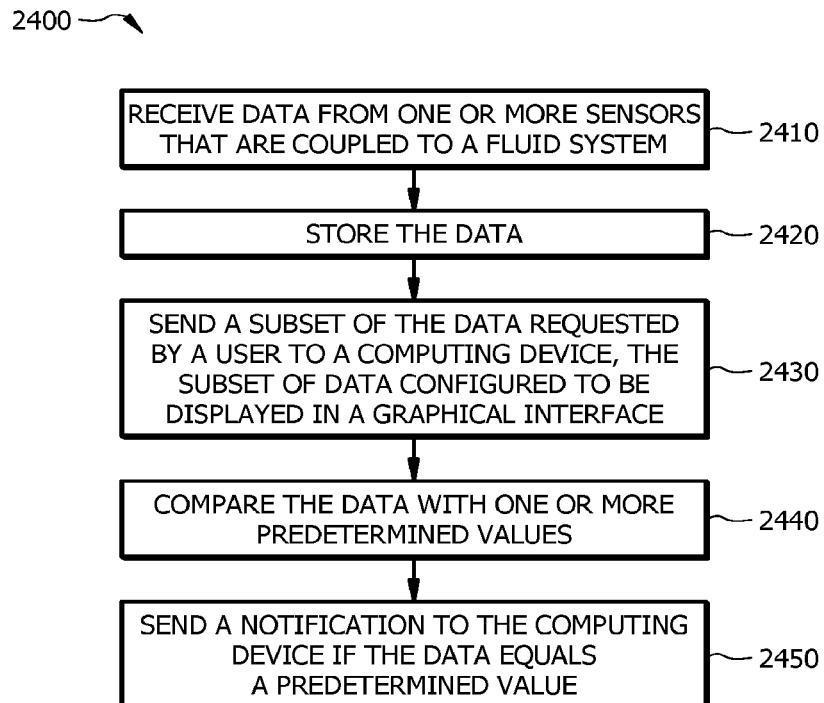
FIG. 24 is a diagram of a possible system embodiment under the present disclosure.

FIG. 24 displays a possible method embodiment 2400 under the present disclosure. At 2410, data from one or more sensors that are coupled to an HVAC hydronic water system (or other system) can be polled or received. At 2420, the data is stored at one or more servers. At 2430, at least a subset of data that is requested by a user is sent to a computing device, the subset of data configured to be displayed in a graphical interface to the user. At 2440, the data is compared with one or more predetermined values (or set values). At 2450, a notification is sent to the computing device if the data equals a predetermined value. In some embodiments, historical data may be used to adjust the predetermined value. For example, a predetermined failure indicator may be compared to historical data on failure and the predetermined failure indicator may be adjusted up or down.

Figure 25:
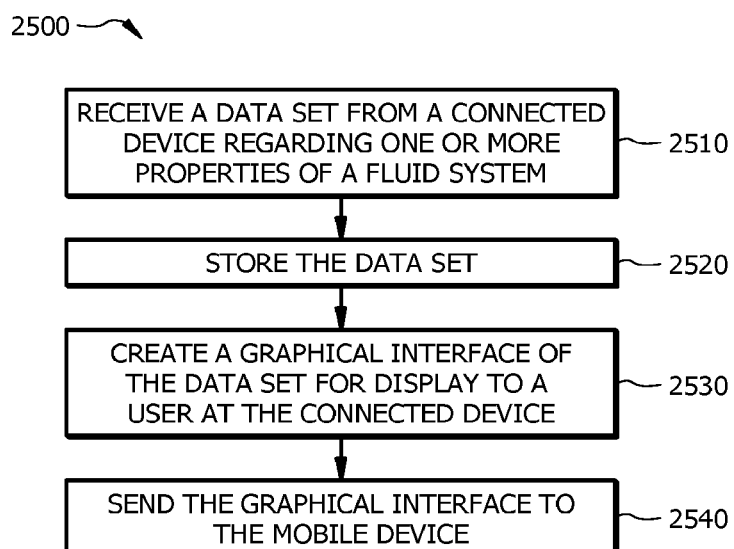
FIG. 25 is a diagram of a possible system embodiment under the present disclosure.

FIG. 25 displays another possible method embodiment 2500 under the present disclosure. At 2510, a data set is received from a mobile device regarding one or more properties of a remote fluid system. At 2520, the data is stored. At 2530, a graphical interface is created of the data set for display to a user at the mobile device. At 2540, the graphical interface is sent to the mobile device.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A system for monitoring a fluid system comprising:
    a plurality of sensors each operable to detect one or more properties of a fluid in the fluid system;
    one or more valves operable to direct the fluid to or from the fluid system;
    one or more injection pumps each connecting a treatment substance reservoir to the fluid system;
    a local controller communicatively coupled to the plurality of sensors, one or more valves and one or more injection pumps and operable to collect and transmit data on the one or more properties of the fluid;
    one or more servers operable to receive data from the local controller and compare the one or more properties of the fluid sensed by the plurality of sensors to one or more target values and to notify a user when a property differs from the target value, the one or more servers further operable to provide a status for the fluid system, the status comprising at least the one or more properties sensed by the pluralities of sensors, a state of each of the one or more valves and a status of each treatment substance reservoir; and
    a client portal communicatively coupled to the one or more servers and operable to display the one or more properties of the fluid, the state of each of the one or more valves and the status of each treatment substance reservoir, wherein the user is able to issue a command to change the one or more properties of the fluid using the one or more injection pumps;
    wherein the local controller is further operable to operate the one or more valves and the one or more injection pumps in response to the command.

2. The system of claim 1 wherein the client portal includes a graphical interface.

3. The system of claim 2 wherein the graphical interface includes a five-axis graph, the five axis graph comprising an axis for a solubility index, an axis for a chemical residual, an axis for a steel corrosion rate, an axis for a copper corrosion rate, and an axis for a saturation index.

4. The system of claim 1 further comprising a respective actuator connected to each of the one or more valves, wherein the one or more valves are each operated by the respective actuator connected to the valve.

5. The system of claim 1 wherein the one or more sensors are operable to detect the one or more respective properties such that the one or more servers can measure or calculate a solubility index, a chemical residual, a steel corrosion rate, a copper corrosion rate, and a saturation index.

6. The system of claim 1 wherein the one or more properties are each a chemical, electrical, mechanical or other physical value.

7. The system of claim 1 wherein the respective treatment substance injectable into the fluid by each of the one or more injection pumps is a chemical operable to change an ionic, chemical or physical property of the fluid.

8. The system of claim 1 wherein each of the at least one of the one or more injection pumps and the one or more valves is operable by the one or more servers to maintain a particular fluid property of the one or more properties within a predetermined range of values.

9. A method for managing a at least one fluid in a at least one fluid system, comprising:
    receiving, at one or more servers, data from a local controller, the local controller in communication with one or more sensors that are coupled to the at least one fluid system, the data comprising properties of the fluid in the at least one fluid system;

receiving, at the one or more servers, a status of one or more valves and one or more injection pumps connected to the at least one fluid system, wherein the one or more valves are operable to direct the fluid to or from the at least one fluid system and the one or more injection pumps each connect a treatment substance reservoir to the at least one fluid system;

storing, at the one or more servers, the data from the one or more sensors, one or more valves and one or more injection pumps;

comparing, at the one or more servers, the data with one or more predetermined values;

sending, by the one or more servers, a subset of stored data requested by a user to a client portal, including results of the comparison performed by the one or more servers;

receiving, by the local controller, a command from the user using the client portal to change the one or more properties of the fluid using the one or more injection pumps; and operating the one or more valves and the one or more injection pumps in response to the command to change one or more of the properties of the fluid.

10. The method of claim 9 further comprising sending, by the server, a map of one or more fluid systems of the at least one fluid system for display to the user.

11. The method of claim 10 wherein the map is color coded by alarm conditions for the one or more fluid systems of the at least one fluid system, each alarm condition representing one of the properties of the fluid having a value outside a predetermined range.

12. The method of claim 9 wherein the at least one fluid system is a water treatment system.

13. The method of claim 9 wherein the subset of stored data requested by the user is presented in a graphical interface.

14. The method of claim 13 wherein the graphical interface includes a five-axis graph, the five axis graph comprising an axis for a solubility index, an axis for a chemical residual, an axis for a steel corrosion rate, an axis for a copper corrosion rate, and an axis for a saturation index.

15. The method of claim 9 further comprising creating, by the one or more servers, a preventative maintenance schedule for the at least one fluid system.

16. The method of claim 9 further comprising creating, by the one or more servers, a predictive maintenance schedule for the at least one fluid system.

17. A system for monitoring and treating an HVAC hydronic water system, comprising:

a water reservoir holding water for the HVAC hydronic water system;

a plurality of sensors each measuring a property of the water in the water reservoir;

a plurality of injection points connected to the water reservoir;

one or more valves connected to the water reservoir through the plurality of injection points;

one or more injection pumps connected to the water reservoir through the plurality of injection points;

treatment chemical reservoirs holding treatment chemicals to alter properties of the water in the water reservoir, the treatment chemical reservoirs connected to the water reservoir using the one or more valves and the one or more injection pumps;

a controller electrically connected to the plurality of sensors, the one or more valves and the one or more injection pumps, the controller operable to collect data on the properties of the water from the plurality of sensors and further operable to operate the one or more valves and the one or more injection pumps;

one or more servers communicatively coupled to the controller, the one or more servers operable to compare the one or more properties of the fluid sensed by the plurality of sensors to one or more target values and to notify a user when a property differs from the target value, the one or more servers further operable to provide a status for the fluid system, the status comprising at least the one or more properties sensed by the plurality of sensors, a state of each of the one or more valves and a status of each treatment substance reservoir; and a client portal communicatively coupled to the one or more servers and operable to display the one or more properties of the fluid, the state of each of the one or more valves and the status of each treatment substance reservoir, the client portal further operable to receive a command from the user and to transmit the command to the one or more servers;

wherein the one or more servers are further operable to send the command to the controller to operate the one or more valves and the one or more injection pumps in response to the command.

18. The system of claim 17 wherein the respective property measured by each of the plurality of sensors is a chemical, electrical, mechanical or other physical value.

19. The system of claim 17 wherein each of the at least one of the one or more valves and one or more injection pumps is operable to change an ionic, chemical or physical level of the water by adding a treatment substance from one of the treatment reservoirs.

* * * * *